(12) United States Patent
Li et al.

(10) Patent No.: US 8,439,674 B2
(45) Date of Patent: *May 14, 2013

(54) SYSTEMS AND METHODS FOR INTRA-ORAL DRUG DELIVERY

(75) Inventors: Chunhua Li, Cupertino, CA (US); Wenda C. Carlyle, Silverado, CA (US); Philippe De Smedt, San Ramon, CA (US); Amir Abolfathi, Woodside, CA (US); Eric E. Kuo, San Jose, CA (US); Robert E. Tricca, Danville, CA (US); Jennifer C. Chen, San Francisco, CA (US); Benjamin M. Wu, San Marino, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/324,882

(22) Filed: Dec. 13, 2011

(65) Prior Publication Data

US 2012/0082950 A1    Apr. 5, 2012

Related U.S. Application Data

(63) Continuation of application No. 11/982,301, filed on Oct. 31, 2007, now Pat. No. 8,075,309, which is a continuation of application No. 11/000,282, filed on Nov. 30, 2004, now abandoned.

(51) Int. Cl.
*A61C 3/00*  (2006.01)
*A61C 17/00*  (2006.01)
*A61C 17/02*  (2006.01)

(52) U.S. Cl.
USPC .............................................. 433/24; 433/80

(58) Field of Classification Search .................... 433/80, 433/88–9, 24, 6, 215–8; 128/859–862; 424/422, 424/435; 604/94.01, 187, 264; 601/162–165
See application file for complete search history.

(56) References Cited

U.S. PATENT DOCUMENTS

| | | |
|---|---|---|
| 3,407,500 A | 10/1968 | Kesling |
| 3,503,127 A | 3/1970 | Kasdin et al. |
| 3,600,808 A | 8/1971 | Reeve |
| 3,660,900 A | 5/1972 | Andrews |
| 3,665,770 A | 5/1972 | Sagi et al. |
| 3,683,502 A | 8/1972 | Wallshein |
| 3,704,985 A | 12/1972 | Pickett et al. |

(Continued)

FOREIGN PATENT DOCUMENTS

| | | |
|---|---|---|
| FR | 2 369 828 | 6/1978 |
| WO | 94/10935 | 5/1994 |
| WO | 98/32394 | 7/1998 |
| WO | 9858596 | 12/1998 |

OTHER PUBLICATIONS

Adachi, H., et al. "Effects of topical administration of a bisphosphonate (Risendronate) on orthodontic . . . ". NCBI, National Library of Medicine, PubMed, Aug. 1994, 1 pg.

(Continued)

*Primary Examiner* — Yogesh Patel
(74) *Attorney, Agent, or Firm* — Brooks, Cameron & Huebsch, PLLC

(57) ABSTRACT

Systems and methods are disclosed for intra-oral delivery of drugs.

41 Claims, 12 Drawing Sheets

U.S. PATENT DOCUMENTS

| | | |
|---|---|---|
| 3,733,905 A | 5/1973 | Bremer |
| 3,742,942 A * | 7/1973 | Westline ............... 433/216 |
| 3,848,335 A | 11/1974 | Bergersen |
| 3,860,803 A | 1/1975 | Levine |
| 3,874,084 A * | 4/1975 | Cole ............... 433/141 |
| 3,916,526 A | 11/1975 | Schudy |
| 3,922,786 A | 12/1975 | Lavin |
| 3,950,851 A | 4/1976 | Bergersen |
| 3,968,690 A | 7/1976 | Blouin et al. |
| 4,215,706 A | 8/1980 | Larson et al. |
| 4,253,828 A | 3/1981 | Coles et al. |
| 4,324,546 A | 4/1982 | Heitlinger et al. |
| 4,324,547 A | 4/1982 | Arcan et al. |
| 4,447,164 A | 5/1984 | Berndt |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,591,341 A | 5/1986 | Andrews |
| 4,609,349 A | 9/1986 | Cain |
| 4,611,992 A | 9/1986 | Lokken |
| 4,629,424 A | 12/1986 | Lauks et al. |
| 4,629,429 A | 12/1986 | Horie |
| 4,664,626 A | 5/1987 | Kesling |
| 4,676,747 A | 6/1987 | Kesling |
| 4,713,243 A | 12/1987 | Schiraldi et al. |
| 4,755,139 A | 7/1988 | Abbatte et al. |
| 4,764,377 A | 8/1988 | Goodson |
| 4,768,951 A | 9/1988 | Abiru et al. |
| 4,787,845 A * | 11/1988 | Valentine ............... 433/88 |
| 4,793,803 A | 12/1988 | Martz |
| 4,798,534 A | 1/1989 | Breads |
| 4,834,110 A | 5/1989 | Richard |
| 4,836,778 A | 6/1989 | Baumrind et al. |
| 4,837,732 A | 6/1989 | Brandestini et al. |
| 4,846,165 A | 7/1989 | Hare et al. |
| 4,850,865 A | 7/1989 | Napolitano |
| 4,856,991 A | 8/1989 | Breads et al. |
| 4,861,268 A | 8/1989 | Garay et al. |
| RE33,093 E | 10/1989 | Schiraldi et al. |
| 4,877,398 A | 10/1989 | Kesling |
| 4,880,380 A | 11/1989 | Martz |
| 4,892,736 A | 1/1990 | Goodson |
| 4,936,862 A | 6/1990 | Walker et al. |
| 4,941,826 A | 7/1990 | Loran et al. |
| 4,968,251 A | 11/1990 | Darnell |
| 4,976,954 A | 12/1990 | Kleber et al. |
| 4,978,391 A | 12/1990 | Jones |
| 4,983,334 A | 1/1991 | Adell |
| 4,990,089 A | 2/1991 | Munro |
| 5,011,405 A | 4/1991 | Lemchen |
| 5,017,133 A | 5/1991 | Miura |
| 5,035,613 A | 7/1991 | Breads et al. |
| 5,055,039 A | 10/1991 | Abbatte et al. |
| 5,059,118 A | 10/1991 | Breads et al. |
| 5,064,640 A | 11/1991 | Kleber et al. |
| 5,074,786 A | 12/1991 | Woodward |
| 5,076,791 A | 12/1991 | Madray, Jr. |
| 5,080,583 A | 1/1992 | Hunting |
| 5,085,585 A | 2/1992 | Zimble |
| 5,098,303 A | 3/1992 | Fischer |
| 5,098,711 A | 3/1992 | Hill et al. |
| 5,100,316 A | 3/1992 | Wildman |
| 5,116,603 A | 5/1992 | Friedman |
| 5,125,832 A | 6/1992 | Kesling |
| 5,127,903 A | 7/1992 | Mailot et al. |
| 5,137,449 A | 8/1992 | Goldin et al. |
| 5,139,419 A | 8/1992 | Andreiko et al. |
| 5,139,768 A | 8/1992 | Friedman |
| 5,145,364 A | 9/1992 | Martz et al. |
| 5,160,737 A | 11/1992 | Friedman et al. |
| 5,165,424 A | 11/1992 | Silverman |
| 5,165,913 A | 11/1992 | Hill et al. |
| 5,186,623 A | 2/1993 | Breads et al. |
| 5,194,003 A * | 3/1993 | Garay et al. ............... 433/215 |
| 5,219,625 A | 6/1993 | Matsunami et al. |
| 5,234,342 A | 8/1993 | Fischer |
| 5,240,415 A | 8/1993 | Haynie |
| 5,273,429 A | 12/1993 | Rekow et al. |
| 5,326,685 A | 7/1994 | Gaglio et al. |
| 5,330,357 A | 7/1994 | Keller |
| 5,330,746 A | 7/1994 | Friedman et al. |
| 5,338,198 A | 8/1994 | Wu et al. |
| 5,340,309 A | 8/1994 | Robertson |
| 5,342,202 A | 8/1994 | Deshayes |
| 5,367,478 A | 11/1994 | Hattori |
| 5,368,478 A | 11/1994 | Andreiko et al. |
| 5,376,006 A | 12/1994 | Fischer |
| 5,382,164 A | 1/1995 | Stern |
| 5,395,238 A | 3/1995 | Andreiko et al. |
| 5,403,577 A | 4/1995 | Friedman |
| 5,409,631 A | 4/1995 | Fischer |
| 5,431,562 A | 7/1995 | Andreiko et al. |
| 5,433,952 A | 7/1995 | Sipos |
| 5,437,872 A | 8/1995 | Lee |
| 5,438,076 A | 8/1995 | Friedman et al. |
| 5,446,070 A | 8/1995 | Mantelle |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| 5,513,630 A | 5/1996 | Century |
| 5,528,735 A | 6/1996 | Strasnick et al. |
| 5,533,895 A | 7/1996 | Andreiko et al. |
| 5,534,524 A | 7/1996 | Bonewald et al. |
| 5,542,412 A | 8/1996 | Century |
| 5,542,842 A | 8/1996 | Andreiko et al. |
| 5,549,476 A | 8/1996 | Stern |
| 5,570,686 A | 11/1996 | Century |
| 5,575,654 A | 11/1996 | Fontenot |
| 5,575,655 A | 11/1996 | Darnell |
| 5,584,688 A | 12/1996 | Sakuma et al. |
| 5,587,912 A | 12/1996 | Andersson et al. |
| 5,605,459 A | 2/1997 | Kuroda et al. |
| 5,607,305 A | 3/1997 | Andersson et al. |
| 5,614,223 A | 3/1997 | Sipos |
| 5,639,795 A | 6/1997 | Friedman et al. |
| 5,645,420 A | 7/1997 | Bergersen |
| 5,645,421 A | 7/1997 | Slootsky |
| 5,648,399 A | 7/1997 | Friedman et al. |
| 5,665,332 A | 9/1997 | Mundschenk et al. |
| 5,683,243 A | 11/1997 | Andreiko et al. |
| 5,692,894 A | 12/1997 | Schwartz et al. |
| 5,711,935 A | 1/1998 | Hill et al. |
| 5,719,197 A | 2/1998 | Kanios et al. |
| 5,725,376 A | 3/1998 | Poirer |
| 5,725,378 A | 3/1998 | Wang |
| 5,725,843 A | 3/1998 | Fischer |
| 5,746,598 A | 5/1998 | Fischer |
| 5,759,037 A | 6/1998 | Fischer |
| 5,759,038 A | 6/1998 | Fischer |
| 5,770,105 A | 6/1998 | Fischer |
| 5,770,182 A | 6/1998 | Fischer |
| 5,800,174 A | 9/1998 | Andersson |
| 5,800,367 A | 9/1998 | Saxer et al. |
| 5,840,329 A | 11/1998 | Bai |
| 5,846,058 A | 12/1998 | Fischer |
| 5,849,266 A | 12/1998 | Friedman |
| 5,851,512 A | 12/1998 | Fischer |
| 5,855,870 A | 1/1999 | Fischer |
| 5,861,298 A | 1/1999 | Adams et al. |
| 5,866,058 A | 2/1999 | Batchelder et al. |
| 5,866,432 A | 2/1999 | Sorsa et al. |
| 5,879,158 A | 3/1999 | Doyle et al. |
| 5,880,961 A | 3/1999 | Crump |
| 5,895,360 A | 4/1999 | Christopherson et al. |
| 5,904,718 A | 5/1999 | Jeffries |
| 5,906,811 A | 5/1999 | Hersh |
| 5,922,346 A | 7/1999 | Hersh |
| 5,924,863 A | 7/1999 | Jacobs et al. |
| 5,944,680 A | 8/1999 | Christopherson et al. |
| 5,945,404 A | 8/1999 | Sugai et al. |
| 5,954,869 A | 9/1999 | Elfersy et al. |
| 5,957,686 A | 9/1999 | Anthony |
| 5,964,587 A | 10/1999 | Sato |
| 5,971,754 A | 10/1999 | Sondhi et al. |

| | | | |
|---|---|---|---|
| 5,975,893 A | 11/1999 | Chishti et al. |
| 5,977,087 A | 11/1999 | Pehrson, Sr. et al. |
| 5,985,249 A | 11/1999 | Fischer |
| 5,989,522 A | 11/1999 | Friedman |
| 5,993,413 A | 11/1999 | Aaltonen et al. |
| 5,994,372 A | 11/1999 | Yaksh |
| 6,021,352 A | 2/2000 | Christopherson et al. |
| 6,036,494 A | 3/2000 | Cohen |
| 6,036,943 A | 3/2000 | Fischer |
| 6,044,309 A | 3/2000 | Honda |
| 6,049,743 A | 4/2000 | Baba |
| 6,060,500 A | 5/2000 | Bonewald et al. |
| 6,068,475 A | 5/2000 | Stoyka, Jr. |
| 6,072,100 A | 6/2000 | Mooney et al. |
| 6,074,674 A | 6/2000 | Jay et al. |
| 6,086,855 A | 7/2000 | Fischer |
| 6,089,869 A | 7/2000 | Schwartz |
| 6,093,084 A | 7/2000 | Jefferies |
| 6,099,479 A | 8/2000 | Christopherson et al. |
| 6,109,916 A | 8/2000 | Wilcko et al. |
| 6,120,587 A | 9/2000 | Elfersy et al. |
| 6,123,544 A | 9/2000 | Cleary |
| 6,132,214 A | 10/2000 | Suhonen et al. |
| 6,132,384 A | 10/2000 | Christopherson et al. |
| 6,138,683 A | 10/2000 | Hersh et al. |
| 6,142,780 A | 11/2000 | Burgio |
| 6,146,655 A | 11/2000 | Ruben |
| 6,183,248 B1 | 2/2001 | Chishti et al. |
| 6,183,251 B1 | 2/2001 | Fischer |
| 6,190,165 B1 | 2/2001 | Andreiko et al. |
| 6,206,920 B1 | 3/2001 | Eliaz et al. |
| 6,210,163 B1 | 4/2001 | Cohen |
| 6,217,334 B1 | 4/2001 | Hultgren |
| 6,228,347 B1 | 5/2001 | Hersh |
| 6,267,590 B1 | 7/2001 | Barry et al. |
| 6,287,120 B1 | 9/2001 | Wiesel |
| 6,293,790 B1 | 9/2001 | Hilliard |
| 6,306,370 B1 | 10/2001 | Jensen et al. |
| 6,309,625 B1 | 10/2001 | Jensen et al. |
| 6,328,715 B1 | 12/2001 | Dragan et al. |
| 6,368,576 B1 | 4/2002 | Jensen et al. |
| 6,375,963 B1 | 4/2002 | Repka et al. |
| 6,455,541 B1 | 9/2002 | Bonewald et al. |
| 6,471,970 B1 | 10/2002 | Fanara et al. |
| 6,485,273 B1 | 11/2002 | Goodwin-Johansson |
| 6,485,706 B1 | 11/2002 | McCoy et al. |
| 6,491,037 B1 | 12/2002 | Mortenson |
| 6,495,120 B2 | 12/2002 | McCoy et al. |
| 6,503,539 B2 | 1/2003 | Gestrelius et al. |
| 6,503,955 B1 | 1/2003 | Dobrozsi et al. |
| 6,509,028 B2 | 1/2003 | Williams et al. |
| 6,528,555 B1 | 3/2003 | Nikutowski et al. |
| 6,562,363 B1 | 5/2003 | Mantelle et al. |
| 6,572,543 B1 | 6/2003 | Christopherson et al. |
| 6,573,282 B1 | 6/2003 | Yaksh et al. |
| 6,589,050 B1 | 7/2003 | Mackey et al. |
| 6,607,382 B1 | 8/2003 | Kuo et al. |
| 6,607,387 B2 | 8/2003 | Mault |
| 6,616,444 B2 | 9/2003 | Andreiko et al. |
| 6,623,698 B2 | 9/2003 | Kuo |
| 6,638,219 B1 | 10/2003 | Asch et al. |
| 6,638,241 B2 | 10/2003 | Yerushalmy |
| 6,638,528 B1 | 10/2003 | Kanios |
| 6,648,639 B2 | 11/2003 | Mao |
| 6,682,348 B2 | 1/2004 | Lawter et al. |
| 6,692,771 B2 | 2/2004 | Pather et al. |
| 6,699,384 B2 | 3/2004 | Lin et al. |
| 6,720,009 B2 | 4/2004 | Gestrelius et al. |
| 6,729,878 B2 | 5/2004 | Cohen et al. |
| 6,736,980 B2 | 5/2004 | Moscaritolo |
| 6,772,026 B2 | 8/2004 | Bradbury et al. |
| 6,814,085 B2 | 11/2004 | Brattesani et al. |
| 6,916,463 B2 | 7/2005 | Lee et al. |
| 7,553,157 B2 | 6/2009 | Abolfathi et al. |
| 2002/0004065 A1 | 1/2002 | Kanios |
| 2003/0003421 A1 | 1/2003 | Bestenheider et al. |
| 2004/0018241 A1 | 1/2004 | Houze et al. |
| 2004/0023853 A1 | 2/2004 | Peri et al. |
| 2004/0101801 A1 | 5/2004 | Mao |
| 2004/0115137 A1 | 6/2004 | Verrall et al. |
| 2004/0115587 A1 | 6/2004 | Breining et al. |
| 2004/0158194 A1 | 8/2004 | Wolff et al. |
| 2004/0260234 A1 | 12/2004 | Srinivasan et al. |
| 2005/0043894 A1 | 2/2005 | Fernandez |
| 2005/0089820 A1 | 4/2005 | Allred et al. |
| 2005/0095561 A1 | 5/2005 | Schatzner |
| 2005/0119723 A1 | 6/2005 | Peacock, III |
| 2005/0152850 A1 | 7/2005 | Engebretson |
| 2005/0175959 A1 | 8/2005 | Jodaikin et al. |
| 2006/0115785 A1 | 6/2006 | Li et al. |
| 2006/0116561 A1 | 6/2006 | Tricca et al. |
| 2007/0207434 A1 | 9/2007 | Kuo et al. |

OTHER PUBLICATIONS

Astho, "The Oral Health and Chronic Disease Connection". ASTDD, May 2002, 8pgs.

Charulatha, V., et al. "Dimethyl 3, 3-dithiobispropionimidate: a novel . . . ". NCBI, National Library of Medicine, PubMed, Jan. 2001, 1 pg.

Domon, S., et al. "In situ hybridization for matrix metalloproteinase-1 and cathepsin K in rat root-reabsorbing tissue . . . ". Elsevier Science, Arch Oral Bio, Nov. 1999, 1 pg.

DYNA Dental Canada Advertisement "HY G Toothbrush Positively Removes Plaque". http://www.ionictoothbrush.com/index4.htm, downloaded Nov. 23, 2004, 2 pgs.

Edwards, John G. "A surgical procedure to eliminate rotational relapse". Amer. J. Orthodont., Jan. 1970, pp. 35-46.

Holliday, L.S., et al. "Effects of . . . ". Univ. of Florida Dept. of Orthodontics, College of Dentistry, Research Reports, Biomaterials and Bioengineering, Jun. 2003, pp. 687-691.

Igarashi, K., et al. "Anchorage and retentive events . . . ". NCBI, National Library of Medicine, PubMed, Sep. 1994, 1 pg.

Johnston, Saren, "Sensible Sensors, The Beauty of a New Chemical Sensor . . . ". Insider, Newsletter for Employees of Ames Laboratory, vol. 13, No. 3, Mar. 2002, 3 pgs.

Kaufman, Hershall. "Microsoft Power Point Presentation" Iontphoresis in Dentistry, Feb. 1998, http://www.hsc.sunysb.edu/oralbio/iontohires/, 38 pages.

Kataropoulou, M., et al. "The influence of glycosaminoglycans and . . . ". NCBI, National Library of Medicine, PubMed, Feb. 2003, 1 pg.

Liu, K., et al. "The effect of EBCI Iontophoresis on orthodontic tooth movement in rabbits". NCBI, National Library of Medicine, PubMed, Jun. 1992, 1 pg.

Liu, X., et al. "cAMP-elevating agents and Adenylyl cyclase overexpression promote an antifibrotic phenotype . . . ". NCBI, Am. J. Phsiol., May 2004, 1 pg.

National Inst. of Health. "Saliva". Spectrum Series, http://www.nidr.nih.gov/spectrum/NIDCR2/2grasecg.htm, downloaded Aug. 2, 2004, 4 pgs.

Nicozisis, J.L., et al. "Relaxin affects the dentofacial sutural tissues". Clin, Orthod. Res., Jul. 3, 2000, pp. 192-201.

Odermatt, A., et al. "Identification of Receptor Ligands by Screening Phage-Display Peptide Libraries . . . ". J. Am. Soc. Nephrol. 2001, pp. 308-316.

Rao, C.N., et al. "Influence of Bioflavonoids on the Metabolism and Crosslinking . . . ". Central Leather Research Inst., India, Jan. 1981, pp. 259-270.

Redlich, M., et al. "Gingival Response to Orthodontic Force". Amer. Assoc. of Orthodontists, 1999, pp. 152-158.

Richards Grayson, A., et al. "Multi-pulse drug delivery from a resorbable polymeric . . . ". Nature Materials, vol. 2, Nov. 2003, pp. 767-772.

Science Daily. "New Class of Composite Organic Material Could Put the Muscle . . . ". http://www.sciencedaily.com/releases/2002/09/020919071705.htm, downloaded Apr. 15, 2008, 3 pgs.

Weng, S.E., et al. "The effect of iontophoresis on accelerating orthodontic . . . ". NCBI, National Library of Medicine, PubMed, Dec. 1993, 1 pg.

Shimono, M., et al. "Regulatory Mechanisms of Periodontal Regeneration". Microscopy Research and technique, 2003, pp. 491-502.

St. John, Marie A.R., et al. "Interleukin 6 and Interleukin 8 as potential Biomarkers . . . ". Arch. Otolaryngol Head Neck Surg., vol. 130, Aug. 2004, pp. 929-935.

Sugiyama, Y., et al. "The level of cathepsin B in gingival crevicular fluid . . . ". NCBI, National Library of Medicine, Entrez PubMed, Feb. 2003, 1 pg.

Sung, H.W., et al. "Crosslinking characteristics and mechanical properties . . . ". NCBI, National Library of Medicine, PubMed, Nov. 1999, 2 pgs.

Sung, H.W., et al. "Crosslinking of biological tissues using genipin and/or carbodiimide". Wiley Interscience, Jan. 2003, pp. 427-438.

Waddington, R.J., et al. "Proteoglycans and Orthodontic Tooth Movement". Scientific Section, Journal of Orthodontics, vol. 28, 2001, pp. 281-290.

Wollensak, G., et al. "Collagen crosslinking of human and porcine sclera". NCBI, National Library of Medicine, PubMed, Mar. 2004, 1 pg.

Zhang, H.J., et al. "Activation of Matrix Metalloproteinase-2 by Overexpression . . . ". Journal of Biological Chemistry, vol. 277, No. 23, 2002, pp. 20919-20926.

Zieman, S.J., et al. "Advanced glycation endproduct crosslinking in the cardiovascular . . . ". NCBI, National Library of Medicine, PubMed, 2004, 1 pg.

Andrews, The Six Keys to Optimal Occlusion Straight Wire, Chapter 3, pp. 13-24.

Biostar Operation & Training Manual, Great Lakes Orthodontics, Ltd. 199 Fire Tower Drive, Tonawanda, New York, 14150-5890 (19 pgs.), 2001.

Cardinal Industrial Finishes, Powder Coatings information posted www.cardinalpaint.com on Aug. 25, 2005 (2 pgs.).

Chiappone, "Constructing the Gnathologic Setup and Positioner", J. Clin. Orthod., vol. 14 (1980), pp. 121-133.

Cottingham, "Gnathologic Clear Plastic Positioner", Am. J. Orthod. vol. 55, No. 1 (Jan. 1969), pp. 23-31.

Cureton, "Correcting Malaligned Mandibular Incisors with Removable Retainers", J. Clin. Orthod. vol. 30 (Jul. 1996), pp. 390-395.

Dent-X posted at http://www.dent-x.com/DentSim.htm Sep. 24, 1998 (6 pgs.).

Elsasser, "Some Observations on the History and Uses of the Kesling Positioner", Am. J. Orthod., vol. 36, No. 5 (May 1950), pp. 368-374.

Kamada, et al. "Case Reports on Tooth Positioners Using LTV Vinyl Silicone Rubber", J. Nihon Univ. School of Dentistry, vol. 26, No. 1, (1984), pp. 11-29.

Kamada, et al. "Construction of Tooth Positioners with LTV Vinyl Silicone Rubber . . . ", J. Nihon Univ. School of Dentistry, vol. 24, No. 1, (1982), pp. 1-27.

Kesling, "Coordinating the Predetermined Pattern and Tooth Positioner with Conventional Treatment", Am. J. Orthod. Oral Surg., vol. 32 (1946), pp. 285-293.

Kesling, "The Philosophy of the Tooth Positioning Appliance", Am. J. Orthod. Oral Surg., vol. 31, No. 6 (Jun. 1945), pp. 297-304.

Kleemann, et al. "The Speed Positioner", J. Clin. Orthod., vol. 30 (1996), pp. 673-680.

Kunii, et al. Articulation Simulation for an Intelligent Dental Care System, Displays (1994) 15: 181-188.

Kuroda, et al. "Three-Dimensional dental cast analyzing system using laser scanning", Am. J. Orthod. Dentofac. Orthop., vol. 110, No. 4 (Oct. 1996), pp. 365-369.

Nahoum, "The Vacuum Formed Dental Contour Appliance", The New York State Dental Journal, vol. 30, No. 9 (Nov. 1964), pp. 385-390.

Nippon Dental Review "New Orthodontic device-dynamic positioner (D.P.)—I. Approach to the proposal of D.P. and transparent silicone rubber" (1980) 452: 61-74.

Nippon Dental Review "New Orthodontic device-dynamic positioner (D.P.)—II. Practical Application and construction of D.P." (1980) 454: 107-130.

Nippon Dental Review "New Orthodontic device-dynamic positioner (D.P.)—III. Case reports of reversed occlusion" (1980) 457: 146-164.

Nippon Dental Review "New Orthodontic device-dynamic positioner (D.P.)—Case reports of reversed occlusion" (1980) 458: 112-129.

Nishiyama, et al. "A New Construction of Tooth Repositioner by LTV Vinyl Silicone Rubber", J. Nihon U. School of Dentistry, vol. 19 No. 2, (1977), pp. 93-102.

Proffit, et al. Contemporary Orthodontics (Second Ed.), Chapter 15, Mosby Inc, (Oct. 1992), pp. 470-494.

Raintree Essix, downloaded from internet Aug. 13, 1997 Essix Appliances, 7 pages total.

Richmond, et al. The Development of the PAR Index (Peer Assessment Rating): Reliability and Validity, European Journal of Orthodontics (1992) 14:125-139.

Schroeder, et al. Eds. The Visual Toolkit, Prentice Hall PTR, New Jersey (1998) Chapters 6, 8 & 9, (pp. 153-210, 309-354, and 355-428, respectively).

Shilliday, "Minimizing Finishing Problems with the Mini-Positioner", Am. J. Orthod., vol. 59 (1971), pp. 596-599.

Warunek, et al. "Clinical Use of Silicone Elastomer Appliances", JCO, (Oct. 1989), pp. 694-700.

Warunek, et al. "Physical and Mechanical Properties of Elastomers in Orthodontic Positioners", Am. J. Orthod. Dentofac. Ortho., vol. 95 (1989), pp. 389-400.

Wells, "Application of the Positioner Appliance in Orthodontic Treatment", Am. J. Orthod. vol. 58 (1970), pp. 351-366.

International Search Report, Oct. 29, 2007 (4 pgs).

* cited by examiner

SYSTEMS AND METHODS FOR INTRA-ORAL DRUG DELIVERY

PRIORITY DATA

This application is a continuation of U.S. patent application Ser. No. 11/982,301, filed Oct. 31, 2007, now U.S. Pat. No. 8,075,309, which is a continuation of U.S. patent application Ser. No. 11/000,282, filed Nov. 30, 2004, now abandoned, the entire contents of which are hereby incorporated by reference.

BACKGROUND

The present invention is related to systems and methods for intra-oral drug delivery. As noted in commonly owned U.S. Pat. No. 6,607,382 entitled "Methods and systems for concurrent tooth repositioning and substance delivery," the content of which is incorporated herewith, the repositioning of teeth may be accomplished with the use of a series of removable elastic positioning appliances such as the Invisalign® system available from Align Technology, Inc., the assignee of the present invention. Such appliances have a thin shell of elastic material that generally conforms to a patient's teeth but is slightly out of alignment with an initial or immediately prior tooth configuration. Placement of the elastic positioner over the teeth applies controlled forces in specific locations to gradually move the teeth into the new configuration. Repetition of this process with successive appliances comprising new configurations eventually moves the teeth through a series of intermediate configurations or alignment patterns to a final desired configuration. A full description of an exemplary elastic polymeric positioning appliance is described in U.S. Pat. No. 5,975,893, and in published PCT application WO 98/58596, the content of these documents are incorporated by reference for all purposes.

The appliance is effective in repositioning teeth when it is placed over the patient's teeth. Removal of the appliance for any reason interrupts the treatment plan and lengthens the overall period of treatment. Therefore, removal of the appliance should be minimized for effective and timely treatment. However, a number of dental and periodontal therapies which may be desired or required by the patient may not be effectively utilized while the appliance is in place. Such therapies may be prescribed by a practitioner to improve oral health or they may be requested by the patient for cosmetic purposes.

The '382 patent discloses devices, systems and methods for orthodontic treatment using elastic repositioning appliances while concurrently providing dental and periodontal therapies. Such therapies are traditionally provided with the use of a variety of accessories and devices which are applied when the repositioning appliance is removed from the patient's mouth. The '382 system eliminates the need for such removal and additional devices by incorporating these therapies into the repositioning appliance. United States Patent Application 20040115587, the content of which is incorporated herewith, discloses an orthodontic treatment involving applying force to reposition teeth and administering a tissue remodeling and/or an angiogenic substance(s) to the periodontal tissue surrounding the teeth to be moved. The substance(s) may be delivered before, during, or after the teeth are moved, and the substance(s) may be selectively applied only to those teeth undergoing movement at any particular time. The substance(s) may be applied from the dental repositioning appliance or may be applied separately, either topically or by injection.

SUMMARY

Systems and methods are disclosed for intra-oral delivery of drugs.

Advantages of the system include one or more of the following. The system enables drugs or therapeutic agents to be delivered through the mouth. The system provides ideal drug delivery for certain diseases relating to periodontics, tooth surface, endodontics, and diseases associated with cancer and medical conditions.

For dental diseases, the system is placed so that release of the therapeutic agent occurs in the immediate vicinity of the disease process. As the volume of distribution is limited to the volume of gum pocket or crevice, relatively high concentrations of therapeutic agent can be delivered by devices with small therapeutic agent reservoir capacities. The small amount of therapeutic agent required under these conditions, typically a few milligrams, greatly reduces the effect of the therapeutic agent at distal sites within the body, thereby greatly decreasing the potential for systemic side effects. Thus, a high degree of effectiveness is achieved using a relatively small amount of drug.

DESCRIPTION

Appliance for Drug Delivery

Figure 1:
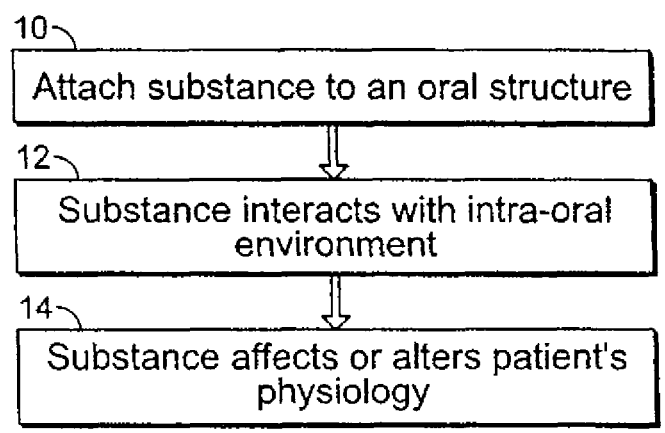
FIG. 1 shows an exemplary method for intra-oral delivery of a substance to an individual.

FIG. 1 shows an exemplary method for intra-oral delivery of a substance to an individual such as a patient, for example. The substance can be a drug or a bio-active agent, among others. The process of FIG. 1 includes attaching the substance to an oral structure (10) and allowing the substance to intra-orally interact with the body of the individual (12). In one embodiment, the substance is fluidly provided from the oral structure into the body at a predetermined rate. The substance eventually affects or alters the individual's physiology in a desired manner (14). The term "oral structure" refers to all areas within the mouth, including teeth, gingiva, cheeks, gums, lips, tongue, thorax, back of the throat, and beneath the tongue.

The method of FIG. 1 thus attaches the substance to an oral structure using a suitable dental device; and fluidly providing the substance from the oral structure into a body at a preselected dose. The substance can accelerate or decelerate tooth movement.

The substance can induce irritation of the oral structure or can induce inflammation of a bone structure. The pattern or sequence of irritation or inflammation can be varied. For example, the pressure, timing, location, degree of irritation or inflammation, and the depth of the irritation or inflammation can be varied.

The substance can be positioned on a bracket, a dental attachment, a bracket auxiliary, a ligature tie, a pin, a bracket slot cap, a wire, a screw, a micro-staple, a denture, a partial denture, a dental implant, a periodontal probe, a periodontal chip, a film, or a space between teeth. The substance can also be positioned on a removable appliance, and one or more modules may be positioned on the removable appliance to house the substance. The substance can provide energy for treatment, for example electric, light, heat, sound, magnetic or electromagnetic energy. The oral structure can be recharged with an additional amount of the same or different substance.

In one embodiment, the physical volume or shape of the substance is computer designed to support a precise delivery of the substance. A computer system can scan a patient's dentition; and design one or more appliances to attach the substance to the oral structure based on the scanned dentition. At least one of the appliances is designed to dispense the preselected dose. Moreover, the appliances can dispense the substance in a predetermined sequence. For example, at least two of the appliances can dispense the substance in two different dosages for delivery at two different periods. Thus, for birth control drugs, more can be delivered on day 15 and less can be delivered on day 30, for example.

The system can perform diagnostics as well. To do this, the system samples an intra-oral substance; and detects a body condition (such as a disease) based on the intra-oral substance. A processor can receive the sampling result and performs a close-loop delivery of substance based on a sampled intra-oral substance, as discussed in more detail below. The system can also transmit the detected body condition to a remote computer for diagnosis.

The substance can be any known chemical substance. Preferably, the substance is a medical grade drug, chemical agent, or a bioactive agent. Examples of the drug or agent can include antibacterials, antibiotics, anti-inflammatory agents, immune-suppressive agents, immune-stimulatory agents, dentinal desensitizers, odor masking agents, immune reagents, anesthetics, nutritional agents, antioxidants, lipopolysaccharide complexing agents, and peroxides, among others.

The attachment of the substance to the oral structure can be done through a removable appliance, a fixed appliance such as a bracket, a dental attachment, a wire, a screw, a tap, a micro-staple, a dental implant, a perioprobe, a periochip, a film or composite material, or a space between teeth, among others.

The tooth is held firmly in place by the cementum, periodontal ligament, alveolar bone and gingiva. These connective tissue structures contain collagen and elastin fibers crosslinked into a supporting matrix. Additional components of this matrix include glycosaminoglycans (GAGs) and proteoglycans which play a role in resisting compressive forces in tissues. The architecture of this matrix can shift over time in response to a constant pressure that stimulates matrix breakdown, matrix resynthesis and remodeling of the tissue. To accelerate tooth movement, agents increase the rate of matrix degradation during the period in which force is applied to the tooth.

Figure 2A:
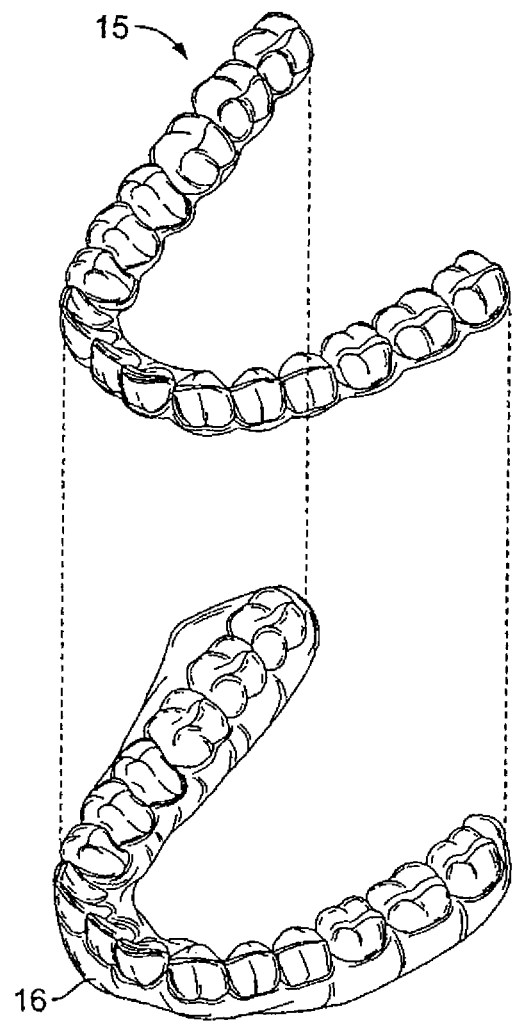
FIGS. 2A-2B are exemplary removable appliances adapted to fit over teeth on a jaw.

FIG. 2A shows an exemplary removable appliance 15 adapted to fit over teeth on a jaw 16. The appliance can be coated with a drug, chemical agent, or a bioactive agent. In one embodiment, the drug is inactive until contact with water or saliva. Alternatively, release of the agent can be stimulated by water or by saliva. Thus, in one case, upon wearing, saliva activates the drug/agent and allows the drug/agent to seep out and treat the patient through the oral cavity of the patient. The substance can also be delivered through the patient's gingiva.

The appliance can release the agent to the oral environment when the appliance is placed over the teeth. Such means may comprise a layer which includes the agent. The layer may be formed over at least a portion of the surfaces of the repositioning appliance. These surfaces include both the cavity surfaces, the surfaces within the cavities which contact the teeth when in place, and the external surfaces, the surfaces of the appliance which contact the cheeks and lips when in place. The layer may be comprised of various materials and may take a variety of forms. For example, the layer may consist essentially of the agent. In other words, the agent may be attached directly to a surface of the polymer shell of an elastic repositioning appliance. This may be achieved by applying the agent (optionally in an inert carrier or diluent) itself to the surface utilizing a number of methods, such as spraying, painting and/or dipping. When the repositioning appliance is placed over the patient's teeth, the agent may then be released to the oral environment.

Alternatively, the layer may comprise the agent present in or on a carrier or binder which promotes adhesion or attachment to the appliance and/or which creates a matrix from which the agent can be released by diffusion or dissolution. In one embodiment, the agent is dissolved in the carrier or binder. In this case, the agent may be provided in powder or similar form and dissolved in a liquid solvent. The result may be a solution which may be applied to a surface of the shell, typically by spraying, painting and/or dipping, to form a coating or film. When the repositioning appliance is placed over the patient's teeth, the agent may then be released from the coating to the oral environment. Release may be due to activation or deactivation of the carrier or any other releasing mechanism, such as by enzymes or proteins in saliva. Or release may be due to degradation of the carrier by contact with, for example, saliva. In some cases, the binder or carrier may evaporate upon application to the layer to the surface leaving the agent behind. In these cases, the agent may be released in a similar fashion as when the agent is directly attached to the surface, as described above. It may be appreciated that any agent, particularly fluoride materials, antibiotics, bleaching materials and breath fresheners, may be delivered to the oral environment in this manner.

In another embodiment, the agent is encapsulated or suspended in the layer. A common material for suspension of an agent is a semisolid material, such as a gel, jelly or putty. Such a material may be applied to a surface of the shell by spraying, painting and/or dipping to form a coating or film. Here, as in all cases, suspension is not limited to a scientific definition and may refer to any situation in which a carrier holds, contains, supports or otherwise includes an agent. Alternatively or in addition, the semisolid material may be deposited in the cavities of the polymer shell which are shaped to receive the teeth. The cavities may be filled to any desired level. When the repositioning appliance is positioned over the teeth, the teeth will directly contact the semisolid material in the cavities and displace any extra material as the teeth are inserted into the cavities. Therefore, it is desired to fill the cavities to a level which will avoid excess overflow of the material from the appliance. Delivery of an agent by use of a semisolid suspension material is common in bleaching treatments and fluoride treatments, for example. However, such treatments apply the material with the use of a tray or generic appliance which does not apply repositioning forces to the teeth. By modifying a repositioning appliance, as described above, orthodontic treatment may continue throughout the delivery of such agents. It may be appreciated that any agent, particularly fluoride materials, antibiotics, bleaching materials and breath fresheners, may be delivered to the oral environment in this manner.

Another common material for encapsulation or suspension of an agent is a controlled-release material. Thus, the layer may be comprised of a rate-controlling material wherein the rate controlling material controls the rate at which the agent is released from the layer. Controlled-release or rate-controlled materials deliver a predetermined amount of an agent at a predetermined rate. Often such delivery maintains a steady-state concentration of an agent in an environment within a desired therapeutic range for a prolonged period of time. Thus, a prescribed dosage may be delivered. In addition, the ability to sustain delivery eliminates the need for repeated applications of the agent for dosed delivery to the oral environment.

Although such controlled release materials may be provided as a semisolid material, such as a gel, jelly or putty, as described above, these materials may also be provided as a solid material which is attached to the polymeric shell of the repositioning appliance. One type of controlled-release material comprises a polymer matrix membrane within which finely dispersed particles of an agent are suspended. The agent may diffuse through the matrix membrane according to a concentration gradient. Alternatively or in addition, the agent may be released by degradation of the polymer matrix membrane material. In either case, the controlled-release material may be provided as a sheet which may be laminated to a surface of the shell. The controlled-release sheet may be layered with the elastomeric polymer and vacuum formed over a mold to form the repositioning appliance. The controlled-release material may be arranged so that it is present on the inside or outside surfaces of the appliance depending on the material and desired application. Or, the controlled-release sheet may be laminated or bonded to a surface of the polymeric shell after forming to supply agent delivery in desired areas. Alternatively, the controlled-release material may be provided as a tablet or similar mass which may be inserted into the polymeric shell of the repositioning appliance. The agent may then elute from the tablet into the oral environment over time.

In another embodiment, the agent may be held within pores of a material and may elute out at a controlled rate from the pores. The agent itself may be absorbed into the pores of the material, or the agent may be suspended in a carrier which is absorbed into the pores of the material. In the latter case, the agent may be released from the carrier by diffusion and/or by controlled degradation of the carrier material. This may incorporate a rate-controlling mechanism in addition to the controlled-release of the agent from the pores. As mentioned, in some cases, enzymes in the patient's saliva will activate the release or degrade the carrier material to release the agent. It may be appreciated that the agent may be released by a combination of any of the release methods.

In a further embodiment, the polymeric shell of the repositioning appliance itself comprises a controlled-release material containing the agent. In this case, at least a portion of a polymeric shell is formed from a controlled release material wherein the rate controlling material controls the rate at which the agent is released from the shell. As previously described, the controlled-release material may be provided in the form of a sheet. Thus, the sheet of controlled-release material may be vacuum formed over a mold of the patient's teeth to form a repositioning appliance itself. In this manner, no additional elastomeric materials may be needed to form the appliance. The controlled-release material may be a polymer matrix membrane, a porous material or any suitable material. Controlled-release may be designed so that the elution rate of the agent corresponds to the repositioning rate of the teeth. The agent may elute throughout the repositioning process, concluding as the teeth reach the desired arrangement prescribed by the appliance.

In another embodiment, the appliance is made from a polymeric material that exhibits reduced stress relaxation and creep when used as a tooth positioner in the oral cavity. Tooth positioners are made from polymeric materials. Once fabricated the tooth positioners are coated with a thin layer of a polymeric material. This coating serves to protect the tooth positioner from the potentially harmful environmental effects of salivary components, water and temperature. The physical properties of the polymeric coating (e.g, durometer, lubricity, elasticity, etc.) may be adjusted by modifying the polymer chemistry. Furthermore, a wide variety of substances may be combined with the polymeric coating solution to provide ancillary patient benefits. For example, flavorants may be combined with the polymeric coating and released over time to help control oral malodor. Drugs to control gingivitis or treat periodontal disease may also be combined with the polymeric coating. Finally, biocompatible dyes or colorants contained in the polymer matrix may be released when exposed to salivary fluids. The gradual disappearance of the colorant may signify whether or not the tooth positioner is being worn by the patient. The polymeric coatings applied to the dental appliance serve as a protective barrier to the harmful effects of salivary components, temperature and water and can contain flavorants, dyes, polymers, surface active molecules, antimicrobial agents and drugs.

In a still further embodiment, the releasing means coupled to at least some of the repositioning appliances comprises a reservoir formed in the shell of the appliance in addition to the cavity which receives the teeth. Typically, a rate controlling membrane is disposed over the reservoir wherein the rate controlling membrane controls the rate at which the substance is released from the reservoir. The reservoir may be pre-filled or preloaded with an agent or substance for delivery. In this case, the appliance may be ready for insertion or use upon removal from any packaging without the need of loading the appliance with the agent for delivery. If the releasing means is designed for a single delivery period, the appliance may be worn throughout the prescribed repositioning period and then disposed of. If the releasing means is designed for multiple delivery periods, the reservoir may be replenished with the agent to be released any number of times throughout the prescribed repositioning period. It may be appreciated that any agent, particularly fluoride materials, antibiotics, bleaching materials and breath fresheners, may be delivered to the oral environment in this manner.

In some instances, it may be desirable to change a visual characteristic of the polymeric shell of an oral appliance. Such appliances comprise a polymeric shell having a cavity shaped to be removably placeable over the teeth and a material on or within the shell that changes a visual characteristic of the shell. Such a change is typically in response to a change in the environment. In some cases, the visual characteristic is a color, such as green, red or blue. Thus, the appliance may appear colored or a particular color under certain environmental conditions, either in the oral environment or when removed. The described material may be a dye which changes color in response to a change in temperature. For example, the dye may change color when the appliance is removed from the mouth and changes temperature from body temperature (37° C.) to room temperature (25° C.). Similarly, the dye may change color when the appliance is rinsed with cool water.

The appliance can be used to provide an intra-oral drug delivery system. In addition to the drugs described above, other compounds can be used as well. For example, a drug coated appliance can be used to deliver desensitizing medication to sensitive teeth. The drug substance can simply be a small amount of the active ingredient in a desensitizing toothpaste or gel, such as Sensodyne®. The desensitizing agent is dispersed throughout the surface of the appliance and is delivered, at a substantially constant rate, to the patient's sensitive teeth for a relatively extended period of time. Although the appliance may be pre-loaded with the agent and ready for use upon removal from any packaging, appliances that are not pre-filled or pre-loaded may require loading prior or immediately prior to placing the appliance over the teeth. Loading may comprise placing the agent in a teeth-receiving cavity. As described previously, the cavities may be filled to any desired level. When the appliance is positioned over the teeth, the teeth will directly contact the agent in the cavities as the teeth are inserted into the cavities. Alternatively, loading may comprise placing the agent into an agent release reservoir in the appliance immediately prior to placing the appliance over the teeth. The agent will then elute from the reservoir into the oral environment when the appliance is in place over the teeth. The elution rate may be controlled by a controlled release membrane which separates the reservoir from the surrounding environment. Loading may also comprise adhering a rate controlling material containing the agent to a surface of the appliance prior to placing the appliance over the teeth. Such a material may comprise a polymer matrix membrane which may be removably or permanently adhered to the polymeric shell of the appliance in desired areas for delivery of the agent. And finally, loading may comprise absorbing the agent into a porous material on or within the appliance immediately prior to placing the appliance over the teeth.

Repositioning of the teeth with the use of a position adjustment appliance involves placing the appliance over the teeth. However, the appliance is periodically removed for daily dental hygiene practices and other events throughout the repositioning protocol until the teeth are moved to at least near the desired tooth arrangement. While the appliance is removed from the teeth, the appliance may be replenished with the agent or substance for delivery. Replenishment may be performed immediately prior to each time the appliance is replaced over the teeth or it may be performed according to any prescribed protocol.

In another aspect, methods for introducing agent delivery to a prescribed tooth repositioning treatment plan are provided. A treatment plan is determined by an orthodontist or practitioner at the outset of orthodontic treatment. The plan involves moving the teeth through a series of intermediate configurations or arrangements to a final desired arrangement with the use of a system of tooth positioning appliances. Each appliance comprises a polymeric shell having cavities which is removably placeable over the teeth and wherein the cavities of successive shells are shaped to reposition teeth from one arrangement to a successive arrangement according to the treatment plan. The entire series of appliances may be provided at the outset of treatment, or a subset of appliances. In any case, the need or desire for delivery of an agent to the oral environment may occur at any point during the course of treatment. In such a case, an agent and/or means for releasing an agent to the oral environment may be coupled to an appliance at any time during treatment.

Means for releasing the agent may include a number of embodiments, including any such means previously described. Typically, means for releasing the agent comprises a layer including the agent, as previously described, and coupling comprises adhering the layer to at least a portion of a surface of the appliance. When the layer consists essentially of the agent, adhering may involve coating, spraying, dipping or painting the agent on the surface of the appliance. Thus, a pre-formed appliance may simply be coated with the agent prior to insertion in the patient's mouth. When the layer comprises an agent present in or on a carrier or binder, adhering may involve attaching the carrier or binder a surface of the appliance. Similarly, when the agent is encapsulated in the layer, the layer may be attached to the surface of the appliance. The layer may comprise a sheet of rate controlling material wherein the rate controlling material controls the rate at which the agent is released from the layer. In this case, the sheet may be bonded to the surface of the appliance with an adhesive. Alternatively, the sheet may be attached to the surface by press fitting. The sheet and the surface may each be shaped so that they snap or fit together by pressing them together. For example, the sheet may have a formed protrusion and the surface a formed inset, wherein the protrusion fits into the inset when pressed upon the inset and holds the sheet in place. In many instances, the appliance may be porous or have a reservoir which can be loaded with a desired agent at any time the treating professional and/or the patient decide that it is appropriate. For example, an appliance can be immersed in a solution of the agent, allowing the appliance to absorb or adsorb the agent at a particular time.

In addition, the sheet may be pre-formed to a shape adapted for fitting against the surface of the appliance or a surface of the teeth or gingiva. For example, the sheet may be preformed to reflect the shape of the surface of one or more teeth or the gingiva, particularly along the gingival margin. The preformed sheet may then be held against that surface when the sheet is coupled to the appliance and the appliance is placed over the teeth. Coupling may involve any means of attaching the sheet to the appliance. In particular, the preformed sheet may further comprise an adhesive layer which may provide bonding of the sheet to the surface of the appliance.

The material to make the appliance of FIG. 2A can be supplemented with additional fillers such as electrically conducting fillers, magnetic fillers, illuminating fillers, piezoelectric fillers, and/or light sensitive fillers. The material properties of the appliance made with or without these additional fillers such as modulus, electrical resistance, material permeability, and birefringence (degree of orientation of the material or stress), illuminating patterns or patterns under special light sources may change after the appliance is worn over time, as these properties are altered due to changes in structure, organization, and/or spatial spacing between the fillers. For example, it is well established that electrical conductivity of filled composites scales with filler volume concentration according to percolation theory. Therefore, mechanical deformation or thermal expansion of the non-conductive polymer matrix will lead to increased average inter-filler spacing, or decreased filler volume concentration, and consequently decreased electrical conductivity. Examples of electrically conductive fillers include metals, graphite, electrically conductive polymers, semiconductors, and superconductors. These changes in properties can be used as an indicator for compliance and can be diagnosed by instrumentation. Similarly, separation of conductive fillers will also lower thermal conductivity, which can also be measured by instrumentations. If the fillers have magnetic behavior in the presence of external stimulation, such as diamagnetics (Cu, Au, Ag, etc.) and paramagnetics (e.g. Al, Cr, Na, Ti, Zr, etc.); or exhibit intrinsic magnetic properties, such as ferromagnetics (Fe, Co, Ni, etc.), antiferromagnetics (e.g. MnO), and ferromagnetics ($MFe_2O_4$), then separation of the filler spacing due to mechanical deformation of the polymer matrix can also lead to decreases in magnetic properties above the Curie temperature. Mechanical deformation of composites with illuminating fillers, such as those that exhibit luminescence, fluorescence, or phosphorescence, will result in decreased illumination intensity. Bending deformation or displacement of piezoelectric fibers can result in electrical potentials which can be either measured, or used to activate other electrically driven indicators (e.g. low power LED light). Fillers with optical properties which depend on external electric field, for example those that shift their absorption coefficients in the UV, IR, or visible spectrum can also serve as indicators of matrix deformation.

Figure 2B:
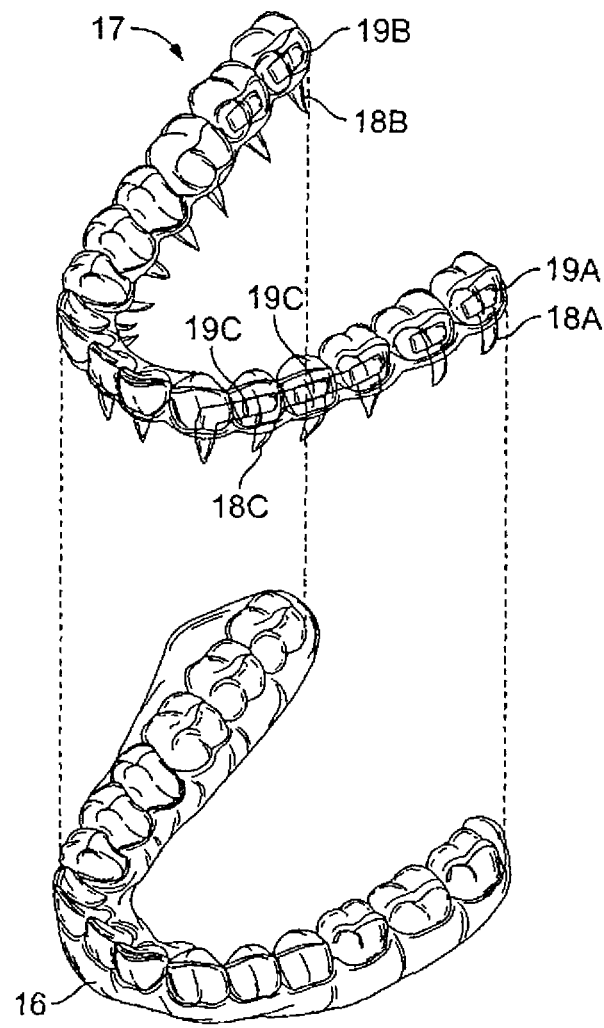

FIG. 2B shows a second embodiment of FIG. 2A. In this embodiment, an appliance 17 has a plurality of delivery nozzles 18A-18C that project from the appliance 17 to contact the patient's gum tissue on the side of the gum or in a periodontal pocket. The nozzles 18A-18C can be on either the frontal side, the lingual side, or both sides of the teeth on the jaw 16. Optionally, one or more reservoirs 19A-19C can store extra drug/agent for delivery through nozzles 18A-18C. In one embodiment, reservoirs 19A, 19B, and 19C can contain the same drug or substance. In another embodiment, reservoirs 19A, 19B, and 19C can each contain a different drug/substance. In yet another embodiment, reservoir 19A and 19C can contain the same drug and reservoir 19B can contain a different drug/substance. The combination of drug storage as discussed above is illustrative only and any suitable combination for storing a plurality of drugs or substances in a plurality of reservoirs 19A-19C can be used.

Figure 2C:
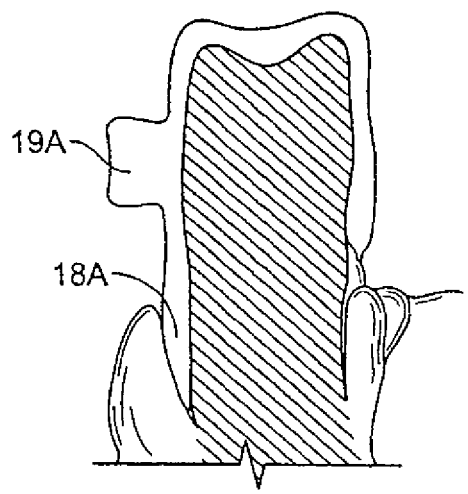
FIG. 2C shows a cross-sectional view of the appliance of FIG. 2B on an exemplary tooth.
Figure 2D:
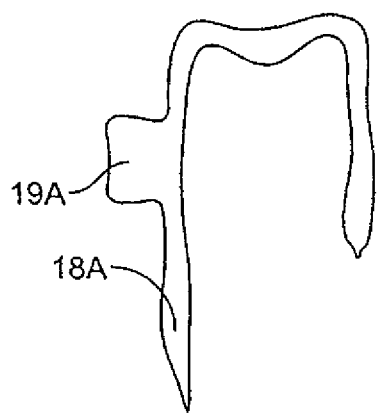
FIG. 2D is a cross sectional view of FIG. 2C without the tooth and gum line.

FIG. 2C shows a cross-sectional view of the appliance of FIG. 2B on an exemplary tooth. As can be seen, the nozzle 18A either stores the drug or agent or receives drug/agent from the reservoir 19A. Moreover, the nozzle 18A is adapted to be inserted into the gum of the patient to deliver the drug/agent to the patient. FIG. 2D is a cross sectional view of FIG. 2C without the tooth and gum line.

Figure 2E:
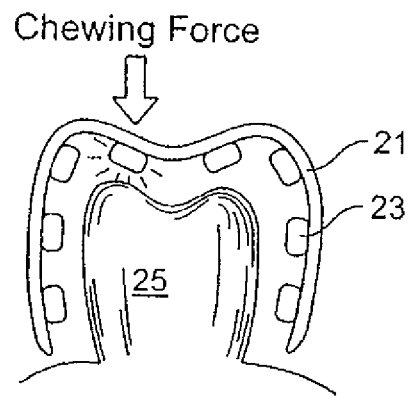
FIGS. 2E-2F show additional embodiments of appliances for delivery of drugs or agents.

Referring now to FIG. 2E, another embodiment of a drug/agent delivery device is shown. In this embodiment, a plurality of drug/agent containers or modules 23 are positioned in an inside lining of a removable dental appliance 21. The appliance 21 is fitted over a tooth 25. During chewing or other oral activities, the appliance 21 carrying the modules 23 is pressed toward the tooth 25. At a predetermined pressure or force, one or more of the modules 23 burst, releasing the drug or agent into the oral cavity. In addition to being positioned inside the lining of the appliance 21, the modules 23 can also be positioned on an outside lining of the appliance 21 as well.

Figure 2F:
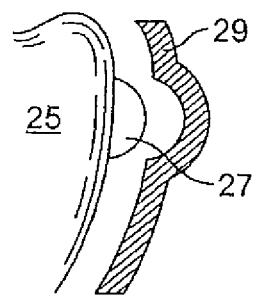

Turning now to FIG. 2F, yet another embodiment of a drug or agent delivery device is shown. In this embodiment, an attachment 27 is mounted on a tooth 25. The attachment contains a first material that is inactive absent the presence of a second material. The second material is coated on an appliance 29 and is also inactive in the absence of the first material. When the appliance 29 is worn over the tooth 25 and the attachment 27, the first and second materials react to form a drug or an agent suitable for intra-oral delivery.

Figure 3:
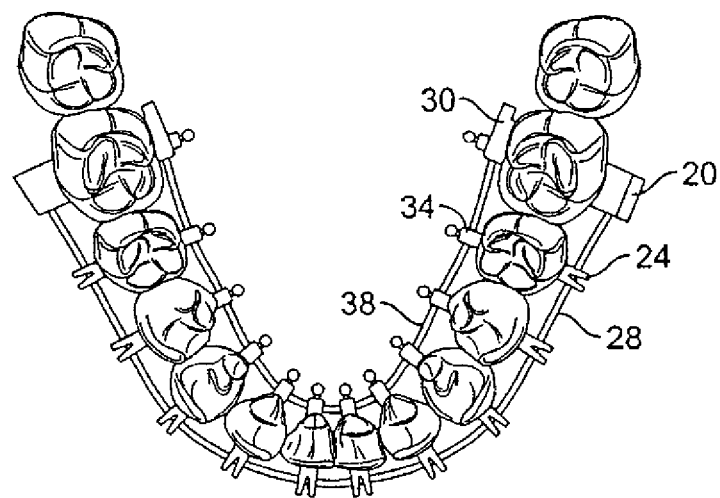
FIG. 3 illustrates another drug delivery system.

Referring now to FIG. 3, another drug delivery system is shown. In this system, brackets and wires are used to effect tooth positioning as well as drug delivery. On the frontal side of the teeth, a base 20 and a plurality of brackets 24 are positioned on the teeth. Additionally, a wire 28 is positioned in the slots of the brackets 24. The base 20 and the brackets 24 contain drug/agent to treat the patient.

In an alternative embodiment, the fixed appliances can be mounted on the lingual side of the teeth as well. For example, a base 30 and a plurality of brackets 34 are placed on the rear or lingual side of the teeth, and a wire 38 links the base and brackets for orthodontic treatment and drug delivery.

In yet another alternative embodiment, the drug/agent can be delivered using bases and brackets and wires on both sides of the teeth such as that shown in FIG. 3.

Figure 4A:
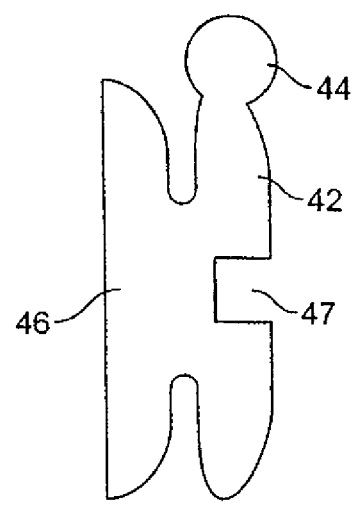
FIGS. 4A-4E illustrate various views of a bracket with a reservoir.
Figure 4B:
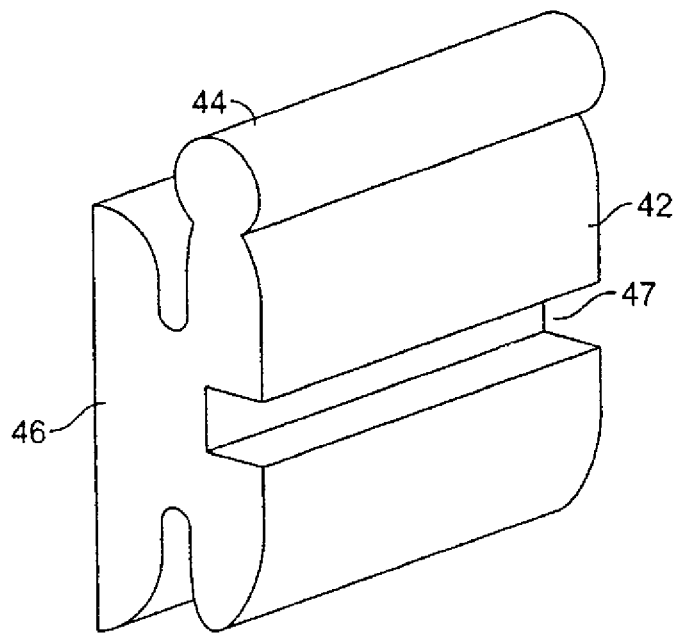

Reservoirs can be positioned on the base and brackets to provide treatment drugs or agents. FIG. 4A shows a cross-sectional view while FIG. 4B shows a perspective view of a bracket with a reservoir. As shown in FIGS. 4A-4B, a bracket body 42 has a base region 46 and a slot 47 to receive a wire (not shown). Above the body 42 is a reservoir 44 that contains drugs or agents for delivery to the patient. The bracket body 42 and reservoir 44 can be of any suitable metal, or can be of a translucent or transparent plastic material or any suitable biocompatible metal. These general types of materials are commonly used in the practice of orthodontic care. It should be understood that the size and shape of the bracket body 42 and reservoir 44 are not critical and the exemplary bracket is described for purposes of illustration.

Figure 4C:
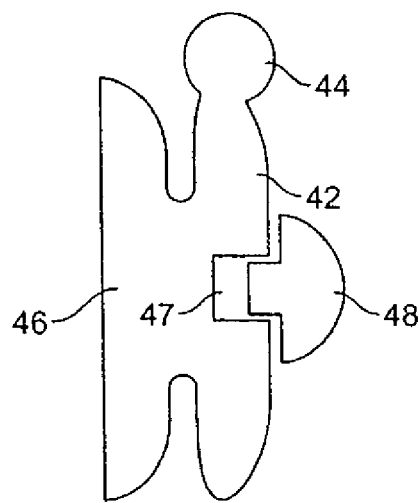

FIG. 4C shows another embodiment where the substance can be stored in a cap 48 that is received by the slot 47. The cap 48 can be used with a conventional bracket without the reservoir 44 as well as with the bracket of FIG. 4A. When used with the bracket of FIG. 4A, the substance in the cap can be the same as the substance in the reservoir 44 or can be different from the substance stored in the reservoir 44.

Figure 4D:
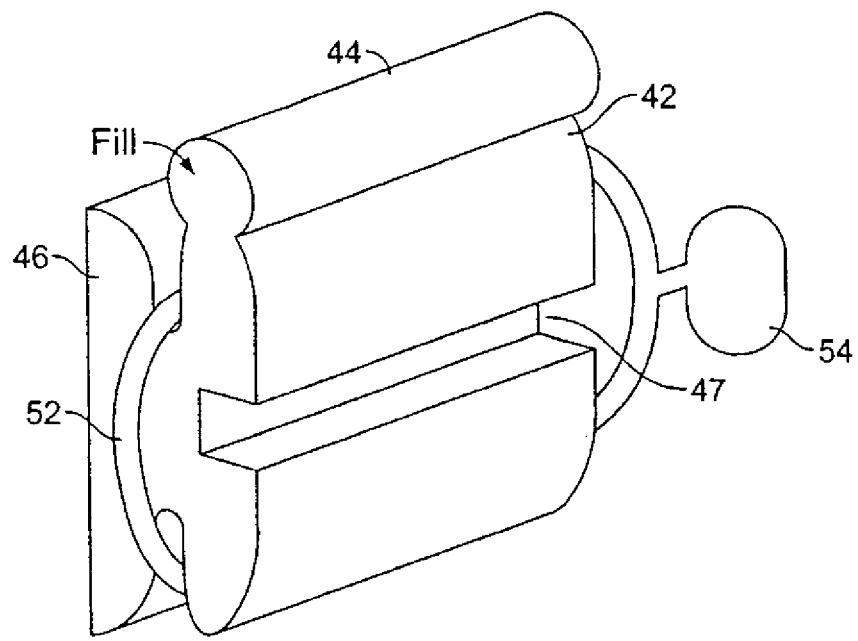

FIG. 4D shows yet another embodiment where the substance can be stored in a band 52 that encircles the slot 47. The band 52 can be used with a conventional bracket without the reservoir 44 as well as with the bracket of FIG. 4A. When used with the bracket of FIG. 4A, the substance in the band 52 can be the same as the substance in the reservoir 44 or can be different from the substance stored in the reservoir 44. Optionally, the band 52 can receive a substance from a band reservoir 54.

Figure 4E:
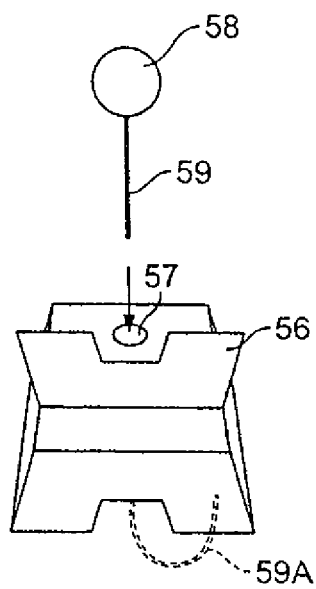

FIG. 4E shows yet another embodiment with a bracket 56 that has an opening 57 extending from one side of the bracket 56 to the other side of the bracket 56. A substance is provided in a housing 58 which can be ball-shaped or box-shaped, among others. A wire 59 is attached to the housing 58 and the wire 59 can be threaded through the opening 57. After reaching the other side of the bracket 56, the wire can be twisted or bent or otherwise secured to the bracket 56, as shown by a bent wire 59A. The bent wire secures the housing 58 to the bracket 56 for delivery of substances to the patient.

Figure 5A:
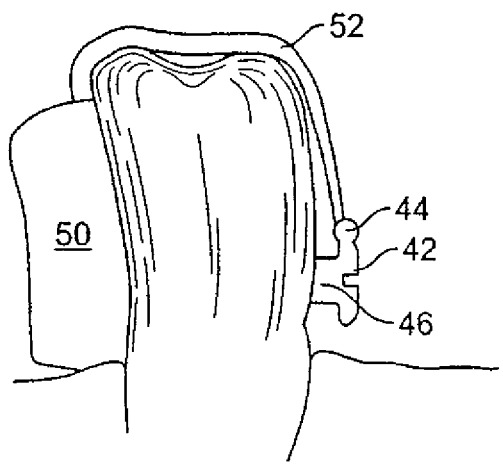
FIGS. 5A-5E show various embodiments of drug delivery systems.

FIG. 5A shows another embodiment where a second reservoir is mounted on a second side of the teeth opposite to the side where the bracket of FIG. 4A is mounted. In this embodiment, a second reservoir 50 contains additional drugs or agents. The second reservoir 50 is connected to the reservoir 44 through a pipe 52 to replenish the drug or agent as needed.

In another embodiment, the reservoirs 44 or 50 can be recharged using a needle to inject additional drug/agent to the reservoirs. Alternatively, the reservoir 44 or 50 can be replaceable to replenish the drug/agent.

Figure 5B:
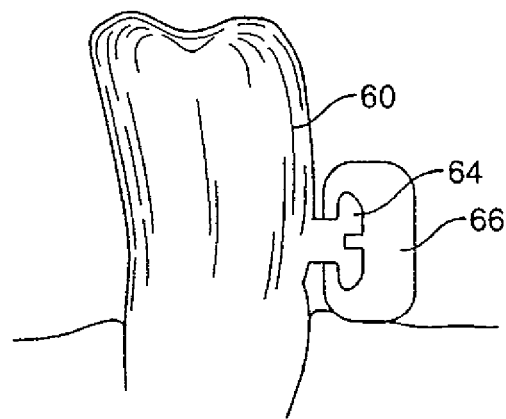

FIG. 5B shows another embodiment where a bracket 64 is used as a mount or support for a drug/agent housing 66 on a tooth 60. In this embodiment, the housing 66 abuts the gum or a surface of the oral cavity to expedite delivery of drug/agent to the patient's body.

Figure 5C:
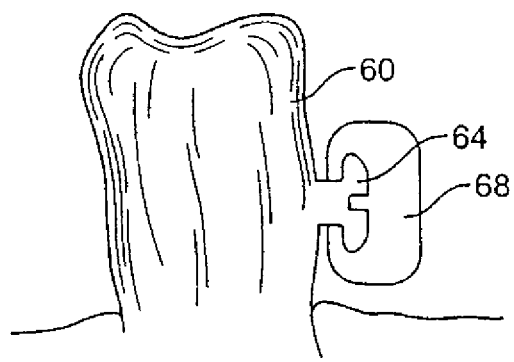

FIG. 5C shows another embodiment where the bracket 64 is used as a mount or support for a drug/agent housing 68 on the tooth 60. In this embodiment, the housing 68 is spaced apart from the gum or a surface of the oral cavity to delivery drug/agent to the patient's body.

Figure 5D:
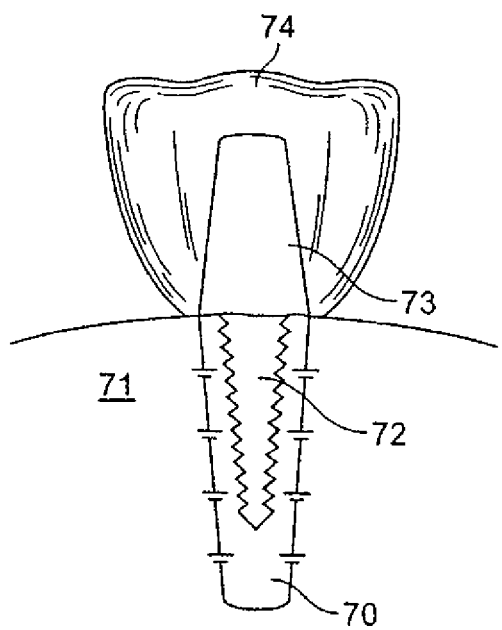

FIG. 5D shows yet another embodiment for delivery of drug or therapeutic agent. A permeable implant 70 is mounted on the patient's gum 71. A post or abutment 73 with a screw or threaded end 72 is mounted on the implant 70. A crown-shaped housing 74 contains a drug or agent that seeps or permeates through the abutment 73 and the implant 70 to be delivered to the patient's body.

Figure 5E:
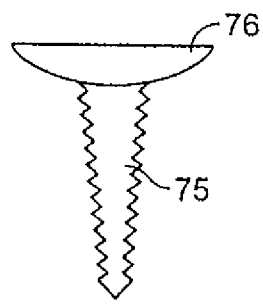

FIG. 5E shows a screw embodiment where drug or agent is embedded in a screw having a head 76 and a threaded portion 75. The screw is tapped into the patient's gum where it delivers the drug or agent into the patient's body. In addition to screws, microstaples can be used to deliver drugs to the body. Moreover, dentures and partial dentures can have drug(s) or agent(s) embedded therein to deliver drug to the patient's oral cavity or body. In addition, the drugs or agents can be embedded in spaces between teeth.

Figure 6A:
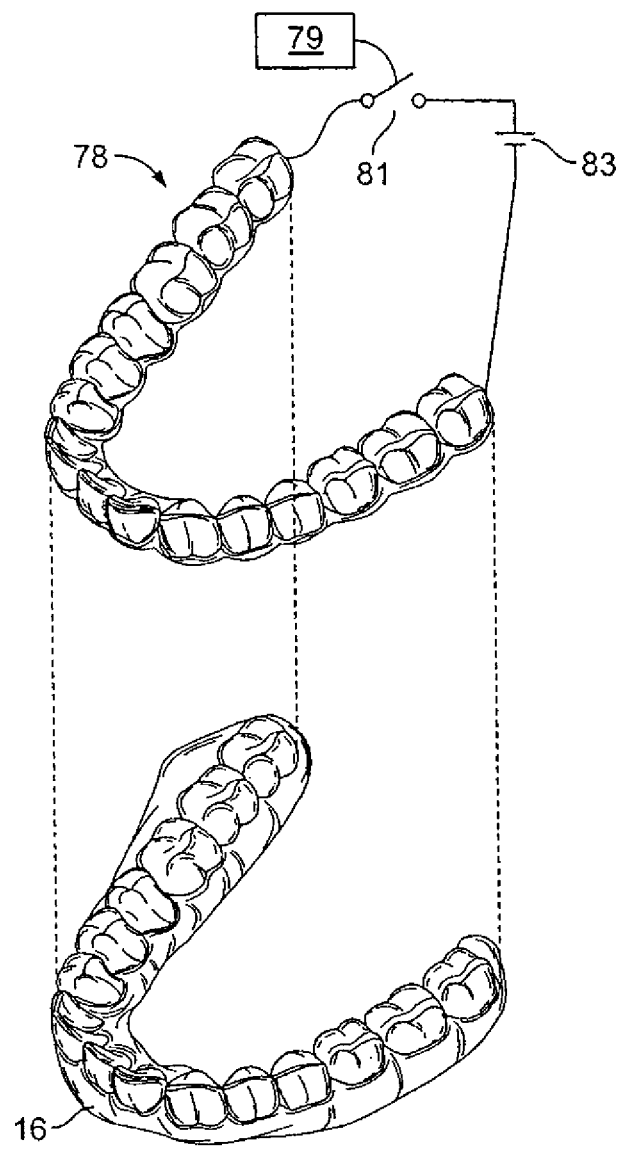
FIG. 6A illustrates an embodiment where energy is applied to an appliance to effect teeth movement or drug delivery.

FIG. 6A shows another embodiment where energy is applied to an appliance 78 to affect teeth movement or drug delivery. In this embodiment, electricity is stored in an energy source 83 such as a battery. A switch 81 is used to deliver energy to the oral cavity. The switch 81 is controlled by electronics 79 such as a microcontroller. The electronics 79 delivers a predetermined amount of energy to treat the patient or to deliver drug.

Figure 6B:
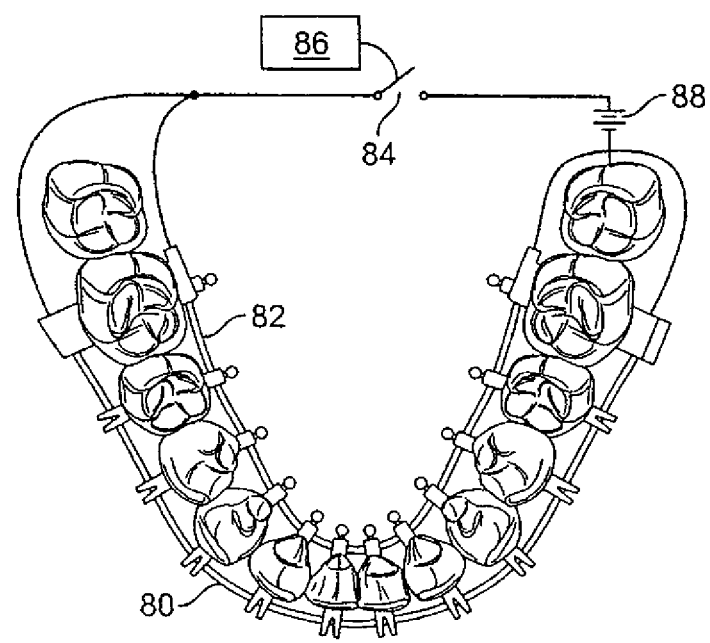
FIG. 6B illustrates an embodiment where energy is applied to wires to effect teeth movement or drug delivery.

FIG. 6B shows another embodiment where energy is applied to wires 80 and 82 to effect teeth movement or drug delivery. In this embodiment, electricity is stored in an energy source 88 such as a battery. A switch 84 is used to deliver energy to the oral cavity through wires 80 and 82. The switch 84 is controlled by electronics 86 such as a microcontroller. The electronics 86 delivers a predetermined amount of energy to treat the patient. The energy in one instance can be low-level electrical current to promote healing at the bone level. In another instance where the energy source 88 is connected through switch 84 to a material such as nichrome, the energy can be low level heat. In another instance where the energy source 88 is connected through switch 84 to a light emitting diode (LED), the energy can be light and when the LED is in a lasing mode, the energy can be a laser beam. The energy can be a magnetic field in another instance where the energy source 88 is connected through switch 84 to an inductor.

Ultra-sound can be used as well where the energy source 88 is connected through switch 84 to an ultrasound vibratory source or transducer. The transducers can be electronically activated to vibrate and emit ultrasonic pulses to promote bone healing. In addition to healing the bone, some of the pulses penetrate the tooth and are returned to other transducers on a sensor array. These echo or reflected pulse signals, after being detected by transducers on the array, can be collected, analyzed and compared to produce a recreation of the tooth or dental structure being examined. By collecting reflected or scattered signals from as many angles as possible, the electronics will have sufficient time-of-flight measurements to perform a tomographic computation to model or map the tooth volume.

Vibrations can be used to inflame or irritate the bone structures to promote tooth movement as well. In one embodiment, the appliance is coated with a material that can expand and contract upon receipt of an electrical stimulus. Electroactive polymer composites, fabricated from an organic filler possessing very high dielectric constant dispersed in an electrostrictive polymer matrix, can be used as dental actuators. The composite can have a matrix made from electrostrictive poly (vinylidene fluoridetrifluoroethylene), an electroactive copolymer and a filler such as an organic semiconductor, copper-phthalocyanine. The composite acts as artificial muscles. Upon actuation, they can repetitively contract and expand to create vibrations on the teeth to encourage teeth movement.

Alternatively, memory-materials such as nitinol can be used and the contraction/expansion can be controlled. Heat, electrical, or microwave energy can be used on other materials to induce them to change state and to inflame or stress the bone/gum structure to induce teeth movement.

In another embodiment, a wire can be attached directly to the teeth or indirectly to the teeth using a removable appliance and the wire can be repetitively wound and unwound using a micro-motor. Such repetitive movements apply stress that inflame or irritate the gum or bone structure to enhance teeth movement.

Thus, as discussed above, FIGS. 6A-6B show that the substance (in this case battery 83 or 88) provides energy to the oral cavity. The energy can be physical, electric, light, heat, sound, magnetic or electromagnetic energy.

In addition to injecting energy, the devices of FIGS. 6A-6B can be used to irritate or inflame the oral structure. For instance, the devices can be used to inflame gingival or the bone structure of the teeth to encourage teeth repositioning.

In another embodiment, the appliances can be used to enhance drug delivery by using electrical current to induce drug movement. For example, the drug molecules can be transported between one electrical pole to another electrical pole. Another implementation provides a positive current on one side of the appliance, and a negative current on the other side of the appliance to force the drug through the gum or dental tissue.

In another embodiment, the appliance induces a change in the polarity of the teeth. The tooth is normally negatively charged and the drug in the appliance is positively charged. Opposite charges attract and bond to each other and the drug or agent can be attached to the tooth surface by "ionic bonding".

In yet another embodiment, the appliance containing drug can be configured so that positively charged ions are transferred to the teeth. The tooth polarity changes from negative to positive. The positively charged tooth ions repel the positively charged ions from other substances. For example, plaque ions are repelled from tooth ions such that plaque can be removed from the oral cavity.

In yet another embodiment, the appliance applies submucosal iontophoresis to accelerate tooth movement. Iontophoresis stimulates osteoclasts in the periodontal pression side and osteoblasts in the tension side.

Agents to Accelerate or Decelerate Movement

In one embodiment, the substance accelerates tooth movement by degrading the matrix. Matrix degradation can be stimulated either directly or indirectly. Chemical agents may act as enzymes to directly breakdown structural proteins in the matrix. Proteases degrade protein, elastases degrade elastin, collagenase degrades collagen, among others. Other drugs or hormones such as relaxin, estrogen, or nicotine may act on cells within the matrix and cause those cells to secrete endogenous matrix degrading enzymes. Many of these naturally occurring enzymes are known as matrix metalloproteases (MMPs) and in the periodontal space these enzymes include MMP-1, MMP-2, MMP-3, MMP-8, and MMP-9. The expression and function of these enzymes is usually under tight control, in part, by a concomitant expression of a group of molecules known as tissue inhibitors of matrix metalloproteases (TIMPs).

A large number of drugs have been developed to prevent matrix breakdown. These drugs are typically useful as anti-inflammatory agents or anti-cancer therapies. Some of these candidates have been used to prevent or treat periodontitis. A very few drugs are available to stimulate matrix breakdown and those are commonly used for indications like wound debridement, breakdown of blood clots, or stimulating gastrointestinal digestion. Their utility in the setting of orthodontic remodeling would need to be tested in appropriate preclinical models.

One exemplary drug can be Granulex or Xenaderm™ whose active ingredient is trypsin. This drug is indicated for wound debridement, wound healing, or varicose vein treatment. This ingredient breaks down many different types of protein. Alternatively, another active ingredient such as hyaluronidase can be used to degrade hyaluronan which is thought to have a role in resisting compressive forces in tissue. Also, elastase can be used to degrade elastin preferentially and may help to both accelerate remodeling and prevent relapse.

Another exemplary drug can be Alteplase or Activase® whose active ingredient is tissue plasminogen activator. These drugs are indicated for thrombolytic therapy. In the presence of a thrombus Activase binds to fibrin and converts plasminogen to plasmin to stimulate fibrinolysis. These drugs may only work in the context of blood clots.

Examples of other exemplary drugs are Arco-Lase®, Creon®, Kutrase®, Kuzyme®, Ultrase®, and Viocase®, whose activity depends on a combination of enzymes: amylolytic, proteolytic, celluloytic and lipase. These drugs are indicated for the treatment of gastrointestinal disorders due to poor digestion. The drug, Arco-Lase, comes in soft, mint flavored tablets. All these drugs warn that they may irritate oral mucosa, which may be an indication that they could work to soften gum tissue as well as degrade food proteins.

Examples of other exemplary drugs are Accuzyme®, Gladase®, and Panafil® whose active ingredient is papain. This drug is indicated for treatment of wound debridement. Papain combined with urea dissolves non-viable protein but supposedly leaves viable tissue intact.

Another exemplary drug can be Potaba® whose active ingredient is aminobenzoate potassium. This drug is indicated for antifibrosis therapy for scleroderma, Peyronie's disease, dermatomyositis and morphea. This ingredient is part of the vitamin B complex and is reported to soften tissue with long term use.

Another exemplary drug can be Aldurazyme® or Laronidase, whose active ingredient is alpha-L-iduronidase. This drug is indicated for treatment of mucopolysaccharidosis. This ingredient is a lysosomal hydrolase that breaks down the glycosaminoglycans: dermatin sulfate and heparan sulfate.

Another class of enzymes that may help to loosen gum tissue for the purpose of accelerating tooth movement is the elastase family of enzymes that break down elastin. Addition of these enzymes or induction of endogenous elastase activity could also serve to prevent tooth relapse following successful orthodontic tooth movement. Elastase enzymes are produced by a number of inflammatory cells for example neutrophil elastase, leukocyte elastase, granulocyte elastase or macrophage elastase (which is also called MMP-12). As described below, agents or activities that stimulate inflammation, cause an increase in the local concentration of these inflammatory cells and therefore an increase in the local concentration of elastase enzymes.

Additional enzymes that would also augment tissue degradation include hyaluronidase and cathepsin. Hyaluronidase is an enzyme found in mucous membranes that specifically degrades hyaluronic acid which is part of the glycosaminoglycan matrix molecules important for resisting compressive force. The cathepsin family of lysosomal enzymes is a large and varied family of cystein proteases important in many disease processes that involve tissue disruption. Cathepsin B, for example, is known to play a role in demyelination, emphysema, rheumatoid arthritis and neoplastic infiltration. Cathepsin B is also known to be elevated in gingival crevicular fluid during orthodontic tooth movement and is thought to be involved in extracellular matrix degradation in response to mechanical stress. Another cathepsin, cathepsin K, is upregulated in odontoclasts and osteoclasts during tooth movement and may play a role in root resorption during this process.

In general, the addition of any enzyme that is capable of breaking down a component of the gingival extracellular matrix is capable of accelerating tooth movement. An alternative means to disrupt the tissue matrix is by addition of compounds that can interfere with the normal interaction between different components of the matrix architecture. For example, a family of proteins known as integrins serve to link cells to the extracellular matrix. Addition of a class of agents known as disintegrins can block this interaction and loosen the connective structure of the matrix. Disintegrins are found in snake venoms and are useful to this species because of their ability to facilitate tissue penetration of the venom. Disintegrins found in many snake species are called variously albolabrin, applagin, batroxostatin, bitistatin, echistatin, elegantin, flavoridin, halysin, kistrin, triflavin, and trigramin.

Primary constituents of the extracellular matrix are collagen, elastin, fibronectin, laminin, integrins, proteoglycans and glycosaminoglycans. Additional constituents are fibrillin, versican, link protein, entactin, tenascin, vitronectin, decorin, cadherin and many others. Many of these components bind to one another to add rigidity and structural integrity to the tissue matrix architecture. Often these interactions are through specific binding sites involving an RGD (arginine-glycine-aspartate) peptide sequence. Antibodies or other binding agents that target these binding sites are capable of disrupting matrix integrity and loosening the tissue. Specific antibodies have been developed to all of these matrix proteins, though only the subset of enzymes that target epitopes important in protein-protein interactions are likely to cause tissue matrix disruption. Antibodies or other binding agents will be effective if they have an affinity for the binding sites that is greater than that of the native proteins. One means of generating a large number of agents capable of binding at, for example, an RGD site is by screening with phage display peptide libraries such as described in Odermatt et al.

Tissue extracellular matrix degradation may be brought about by direct application of enzymes and binding agents as described above, or through indirect means by addition of agents that stimulate the overexpression of endogenous enzymes. An example of this type of agent includes drugs that alter the expression or activity of matrix metalloproteases (MMPs). MMPs are a family of structurally related, protein-degrading enzymes that require calcium ions for structural conformation and zinc ions in their active site for function. The MMP enzymes can be administered either alone or in combination to directly impact tissue degradation. As mentioned previously, MMP-1, MMP-2, MMP-3, MMP-8 and MMP-9 are the matrix degrading enzymes known to be active in the periodontal space. Matrix metalloproteases are also known as matrix metalloproteinases, collagenases, gelatinases, or CLGs. For example, depending on the nomenclature used, MMP-2 is also called collagenase type 4 (A), gelatinase A, or CLG 4 (A). Some MMPs are known by additional names due to the fact that their discovery preceded knowledge of the family characteristics. For example, MMP-3 is also known as stromelysin-1 or transin. The MMP enzymes listed above have been purified and are available commercially.

Collectively, the MMP family of enzymes is capable of digesting almost all of the components of the extracellular matrix. They often work best in concert whereby an MMP isotype with selective collagenase activity will cleave the type 1 collagen triple helix allowing access to additional MMP enzymes which then further degrade the protein. MMP-3, in contrast to MMP-1 and MMP-2 does not break down type I collagen but can degrade proteoglycan and fibronectin which are other important constituents of the extracellular matrix. As they occur naturally in periodontal tissue MMP activity is finely balanced by the presence of endogenous enzyme inhibitors known as tissue inhibitors of metalloproteases (TIMPs). Adding exogenous MMPs to the tissue can alter the balance of activity to bring about relatively more matrix degradation and tissue disruption that may aid in tooth movement.

An exemplary drug that may work to accelerate tooth movement by stimulation of endogenous MMP activity is Prepidil® (dinoprostone) whose active ingredient is prostaglandin E2. This drug is indicated for treatment of induction of labor. Prostaglandin E2 has been shown to enhance MMP-1 (collagenase) and sometimes MMP-3 (stromelysin) expression in human gingival tissue. Another exemplary drug that contains the same active ingredient is Prostin E2® which is indicated for termination of pregnancy.

Another exemplary drug can be Fluprostenol. This drug is a potent luteolytic agent with prostaglandin F2alpha activity. Research shows that it can increase MMP-1 production and degrade connective tissue in human gingiva.

Another exemplary drug can be Nicoderm®, Commit® and Nicorette®, whose active ingredient is nicotine. This drug is indicated for treatment of smoking cessation. This ingredient has many effects such as vasodilation, but research shows it can increase collagenase activity and matrix turnover in gingival tissue.

Another example of an agent that stimulates the overexpression of endogenous enzymes is keratinocyte-derived collagenase stimulatory factor also known as stratifin. Delivery of this agent can cause upregulation of collagenase enzymes in fibroblasts present in gingival tissue. An even more direct way to stimulate overexpression of matrix degrading enzymes is to use gene therapy techniques to either transfect local cells with constructs encoding these enzymes or with enhancer or promoter elements capable, of stimulating endogenous gene transcription of those particular enzymes. For example, overexpression of manganese superoxide dismutase is known to cause activation of MMP-2. Agents that elevate the intracellular concentration of cyclic adenosine monophosphate (cAMP) are also capable of promoting MMP-2 overexpression, increasing the activity of this enzyme and decreasing collagen content in tissue. Examples of agents with this capability are isoproterenol, prostaglandin E2 and forskolin. Relaxin is another agent that is capable of enhancing MMP-2 production.

In general any agent that triggers an inflammatory response can bring about stimulation of MMP overexpression and matrix degradation. Another large family of molecules of interest in this regard is the cytokine family of molecules. Cytokines are agents usually secreted by cells to bring about a response in another cell. Thus, they are important in cell to cell communication. A number of common inflammatory cytokines have been elucidated and many more are likely to be discovered and characterized in the future. Inflammatory cytokines are released after injury and help to recruit additional inflammatory cells into the area of tissue damage. Orthodontic tooth movement usually involves a mild inflammatory response. If exacerbated, this inflammatory response will likely promote additional tissue degradation and may speed the process of tooth movement. The most commonly known inflammatory cytokines are interleukin-1 (IL-1), interleukin-6 (IL-6), tumor necrosis factor-alpha (TNFa) and transforming growth factorbeta (TGF-$\beta$).

There are many ways to stimulate an inflammatory response beyond direct addition of inflammatory cytokines. Inflammation can be brought about by virtually any means of causing local tissue damage. Mechanical force such as pushing, pulling or stretching the tissue can trigger release of local pro-inflammatory cytokines. Tearing or abrasion of either soft tissue or bone can similarly trigger an inflammatory reaction. Addition of an irritant such as a powder, polymer, or any type of foreign body can incite inflammation. Alteration of local pH into either an acidic or basic range beyond normal physiological pH can cause inflammation. Elevated temperature can have a similar effect as can the addition of other energy sources such as ultrasound, or electrical energy.

Regardless of what means is used to stimulate the activation of local tissue degrading enzymes there is a need for limiting this activation so as not to cause significant and irreversible tissue damage. What is sought is a mild enhancement of the inflammatory response normally associated with orthodontic tooth movement. The ability and mechanisms by which these limitations can be established will depend on the stimuli used to enhance inflammation. If agents or enzymes are administered directly, their activity can be controlled by monitoring the dose-response relationship and choosing the most appropriate concentration. If indirect stimulators of endogenous enzymes are used then the tissue itself may provide some regulatory feedback (e.g. upregulation of TIMPs) to modulate and limit the overall response. The ultimate goal in this case is to strike the right balance to bring about moderate tissue disruption.

In one implementation, the drug or bioactive agent assists in a "retention" phase, without which there is a tendency for the teeth to return to their initial position (relapse). The underlying cause for this relapse appears to reside in the gingival tissue which, unlike bone and the PDL, is not resorbed during orthodontic treatment but is compressed and consequently retracts. On the pressure aspect of the gingiva there is an increase in the number and size of elastic fibers and an increase in collagen. The elastic forces stored in the compressed gingiva can exert pressure on the tooth and cause relapse after the release of retention. Procedures such as gingival circumferential fiberotomy have been introduced to disconnect the compressed gingiva from the tooth and have demonstrated some success in preventing tooth relapse.

Bioactive agents can accelerate tooth movement. The bioactive agents described above work primarily by enhancing collagen or elastin degradation. If delivered to the appropriate local tissue bed these agents should, then, limit the increase in collagen and elastin accumulation on the pressure side of the gingiva and reduce the tendency to relapse. There are, however, other mechanisms to prevent tooth relapse. One way to chemically stabilize tooth position after completion of the orthodontic movement involves increasing the number of chemical crosslinks between collagen fibers, particularly on the tension aspect of the tooth. Increased crosslinking provides more structural stability to the new fiber orientation in the gingival tissue. Formaldehyde and glutaraldehyde are the most well known agents capable of crosslinking collagen and these agents are commonly used to treat bioprosthetic tissue prior to use of that tissue as a medical implant. Standard formulations of formaldehyde and glutaraldehyde are likely too toxic to be used in situ, but may be modified to reduce their tissue toxicity.

Chemical crosslinking agents can be used to crosslink extracellular matrix components for many different indications. For example, Genipin is a relatively nontoxic, naturally occurring crosslinking agent that can be used. Carbodiimide is considered to be a somewhat less toxic crosslinking agent, though at least one study showed that genipin was better able to stimulate intermolecular collagen crosslinks compared to carbodiimide. Intermolecular rather than intrahelical crosslinks are more likely to bring about the desired tissue stabilization. 1,6-diaminohexane (DAH) is also an effective collagen crosslinking agent that has been shown to be slightly less toxic than cardodiimide especially in the presence of glycosaminoglycans (which are naturally occurring in gingival tissue). Dimethyl 3,3'-dithiobispropionimidate is yet another example of a crosslinking agent reported to be more biocompatible than standard agents like glutaraldehyde Another class of compounds that may be useful is the reducing sugars including glucose, ribose and derivatives of these sugars. The slow crosslinking reaction between reducing sugars and biological amines leads to the development of advanced glycation endproducts (AGEs). AGEs accumulate over the course of a person's lifespan and a number of detrimental conditions have been attributed to this accumulation including increased vascular and myocardial stiffness, endothelial dysfunction, altered vascular injury responses and atherosclerotic plaque formation. In the setting of orthodontic applications, however, increased crosslinking for a limited period of time could prove beneficial and these agents are relatively simple sugars not associated with any additional toxicity. Acceleration of AGE-related crosslinking can be brought about by increasing the concentration of reducing sugars and also by application of external energy such as UV irradiation.

The bioflavonoids is another broad class of compounds that could prove very useful in this endeavor. They are exemplified by molecules such as riboflavin, catechin and rutosides. Many of these compounds are found naturally in food substances like red wine and green tea. They tend to be very biocompatible but are also known to promote the crosslinking of collagen either alone or in combination with adjunctive energy like UV-A or rose Bengal/white-light irradiation. In the case of riboflavin-UVA, this treatment has been used clinically to promote collagen crosslinking of the sclera to increase its biomechanical strength for the treatment of progressive myopia.

Although it appears that the accumulation of extracellular matrix proteins in gingival tissue has an important role in tooth relapse, there is also evidence that bone remodeling plays a part. Experimental data from the School of Dentistry in Tohoku University, Japan, showed the ability of a bisphosphonate (risedronate) to prevent tooth relapse. Risedronate is a potent blocker of bone resorption. When applied topically during the phase of orthodontic tooth movement, it reduced tooth movement. When applied during the retention phase, it was able to inhibit relapse.

In another embodiment, the substance can be anesthetics and analgesics such as benzocaine, lidocaine and prilocaine, among others, that are locally released through the appliance. These substances may promote patient compliance for appliance usage/wear, and also for the palliative relief of oral discomfort due to intraoral ulcers, cancer sores, and other lesions associated with trauma, disease, or surgical procedures.

In yet another embodiment, the drug can be nicotine to relieve patient discomfort or to treat another disease. As discussed in U.S. Pat. No. 4,215,706, the content of which is incorporated by reference, tobacco (donor tobacco) is contacted with a receiving substrate on the appliance which has been treated with a strong acid or an ammonium salt of a strong acid. Part of the nicotine in the donor tobacco is transferred from the donor tobacco to the receiving substrate. Thereafter the donor tobacco and the substrate may be separated. The donor tobacco has a reduced nicotine content for pain relief or medical treatment.

In yet another embodiment, the appliance can be used to provide a local release of breath fresheners such as menthol, peppermints, spearmints, wintergreen, zinc gluconate, citrus, clove and thymol, among others, that may promote patient compliance to facilitate treatment. More breath freshener information is shown in US Patent Publication No. 20040115137, the content of which is incorporated by reference.

Additionally, the substance can prevent tooth decay through fluoride treatment. Treatments include toothpastes, gels, rinses and varnishes. Gum disease, such as gingivitis or periodontitis, is caused by bacterial growth associated with dental plaque and calculus deposits. The most common recommendation for preventing such bacterial growth is to mechanically remove the plaque from the tooth surfaces. However, chronic gingivitis and tooth decay have plagued many individuals who in fact comply with good oral hygiene methods and plaque removal. This may be due to a variety of factors including genetic predispositions, illnesses, mouth breathing, and medical treatment programs. In such cases, bacterial control may be accomplished with the use of antibacterial drugs. A common antibacterial agent shown to be effective in reducing the activity of many common strains of oral flora is chlorhexidine. Chlorhexidine is a cationic biguanide microbicide with a broad spectrum of activity against many forms of bacteria and fungi. Therefore, it has been a popular agent in many studies of gingivitis reversal. Chlorhexidine has traditionally been delivered to the oral environment through the use of rinses, such as Peridex® (Proctor and Gamble). Sustained delivery to the gingiva has also been attempted with the use of chlorhexidine impregnated dental floss and dental appliances, such as trays or mouthguards. Another frequently prescribed antibacterial agent is tetracycline. Tetracycline is a broad spectrum antibiotic which is effective against virtually all common groups of pathogenic bacteria, both gram positive and negative. Tetracycline may be combined with an antifungal agent, such as amphotericin, to provide activity against fungi. Tetracycline has traditionally been delivered to the oral environment through systemic administration, although localized delivery has been attempted with the insertion of tetracycline-filled hollow fiber devices into periodontal pockets and the use of tetracycline laden dental appliances, such as trays and mouthguards. In addition, a number of other antibacterial drugs are available for dental and periodontal therapy.

Cosmetic treatments often include tooth bleaching or whitening and breath freshening products. Discolorations of enamel and dentin may occur due to aging, consumption of staining substances (coffee, tea, colas, tobacco), trauma, staining due to systemic tetracycline (antibiotic) therapy, excessive fluoride, nerve degeneration and old dental restorations. Bleaching lightens these discolorations for a whiter or brighter appearance. Typically, a bleaching gel is placed in a thin custom-fitted tray that fits over the teeth. The tray is worn at night for usually 10 to 14 days and may require periodic rebleaching treatments for approximately one or two nights every six months. Breath freshening products are often used by patients to treat halitosis or for enjoyment of the taste. These include a variety of sprays, rinses, mints, gums, or candies, to name a few.

Additionally, the substance can include chemicals that irritate the gum or bone. Alternatively, the substance can inflame a bone.

Often the use of a combination of drugs or bioactive agents can impart more benefit than the use of any single agent. The appliance used to deliver therapeutic or cosmetic agents to oral tissue can be easily adapted to deliver more than one agent and can also be adapted to deliver specific agents to select locations within the oral tissue. For example, a drug that accelerates collagen and/or elastin degradation might be delivered to the pressure aspect of the gingiva where there is typically an increase in the number and size of collagen and elastic fibers that oppose tooth movement. Simultaneously, the appliance might deliver an agent that promotes the crosslinking of collagen to the tension aspect of the gingiva to help stabilize the tooth movement achieved with the appliance. In one embodiment, reservoirs 19A, 19B, and 19C (FIG. B) can contain the same drug or substance. In another embodiment, reservoirs 19A, 19B, and 19C can each contain a different drug/substance. In yet another embodiment, reservoir 19A and 19C can contain the same drug and reservoir 19B can contain a different drug. Thus, in one example bleaching agents can be stored in one reservoir and delivered to the tooth itself while a second reservoir can store and deliver an agent capable of accelerating tooth movement to the gingiva surrounding the tooth.

Just as different agents need not be delivered to identical locations within the oral tissue, different agents need not be delivered at the same time. It may be advantageous to deliver one agent at the beginning of orthodontic treatment and a different agent at another point during the treatment. An example of this treatment regimen would be delivery of agents to accelerate tooth movement during the first weeks of orthodontia and delivery of agents to prevent tooth relapse following the period of tooth movement.

In some cases it is necessary to add one agent to modify the activity of another agent. For example, a buffering agent may be needed to alter the pH of a drug so as to make the therapeutic agent less caustic. In another case it might be necessary to add one agent to stabilize or activate the therapeutic agent once it has been released from the appliance. An alternative exemplary case would be the use of more than one agent that have the same general effect as, for example, two agents that are likely to accelerate tooth movement. Two or more agents may be employed rather than one either because they will act synergistically by employing different modes of action to bring about an effect or because they have different unwanted side effects that can be reduced by lowing the dose delivered of each but maintaining a beneficial therapeutic effect because of the ability of the agents to work together in concert.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow. For example, although films or appliances have been disclosed as mechanisms for delivery drugs or substances, droplets can be used to deliver substances to the patient as well. Typically, droplets can be sized within the range of about 1 to 200 microns and may be presented to the mucosa within a liquid, solid, or gaseous suspension, including an aerosol system which refers to a gaseous suspension of particles dispensed within the form of a mist. Other embodiments for delivering drugs or substances can be used as well. Whereas particular embodiments of the present invention have been described herein for purposes of illustration, it will be evident to those skilled in the art that numerous variations of the details may be made without departing from the invention as defined in the appended claims.

What is claimed is:

1. A device for delivering one or more substances, comprising:
    a dental device comprising a shell formed of a material and the dental device configured to move a number of teeth and including one or more reservoirs formed in the shell;
    at least one of the reservoirs supplied with the one or more substances; and
    a nozzle formed of the material as a portion of the shell and connected to the at least one reservoir and configured to be inserted into a gum of a patient to fluidly release the one or more substances from at least one reservoir at a first preselected dose at a first predetermined time period and to fluidly release the one or more substances from at least one reservoir at a second preselected dose at a second predetermined time period, wherein the nozzle is shaped to conform to the gum for prolonged placement therein.

2. The device of claim 1, wherein the one or more substances include a therapeutically effective amount of a drug or a bioactive agent.

3. The device of claim 1, wherein the one or more substances provide one or more results selected from the group of results including:
    accelerating tooth movement;
    decelerating tooth movement;
    accelerating tooth movement by degrading collagen in the oral tissue;
    accelerating tooth movement by degrading elastin in the oral tissue;
    accelerating tooth movement by increasing the expression of endogenous enzymes that degrade collagen;
    accelerating tooth movement by increasing the expression of endogenous enzymes that degrade elastin;
    accelerating tooth movement by increasing the activity of endogenous enzymes that degrade collagen;
    accelerating tooth movement by increasing the activity of endogenous enzymes that degrade elastin;
    accelerating tooth movement by causing degradation of glycosaminoglycans or proteoglycans;
    inducing irritation of the oral structure;
    inducing inflammation of a bone structure;
    inducing inflammation of surrounding tissue;
    inducing inflammation of a bone structure or surrounding tissue by increasing the local concentration of interleukin-1, interleukin-6, tumor necrosis factor-alpha, or transforming growth factor-beta;
    relieving oral pain involved with dental movement;
    relieving pain from alveolar ridge augmentation and orthognathic treatment;
    providing fresh breath;
    altering tooth movement by stimulating bone resorption;
    altering tooth movement by reducing bone resorption; and
    preventing tooth relapse by causing an increase in the number of crosslinks between tissue matrix proteins in the oral environment.

4. The device of claim 1, further configured to deliver one of the one or more substances to a specific location within the gum and to deliver a different one of the one or more substances to a different location within the gum.

5. The device of claim 1, further comprising a supply of energy thereto.

6. The device of claim 1, wherein the energy comprises electric, light, heat, sound, magnetic or electromagnetic energy.

7. The device of claim 1, wherein the device is configured to fluidly release the one or more substances without active physical manipulation of the at least one reservoir.

8. The device of claim 1, wherein the device is designed from scans of the patient's dentition.

9. The device of claim 1, wherein the device is designed to dispense the one or more substances in a predetermined sequence.

10. The device of claim 1, wherein the device is designed to dispense the substance in two or more different preselected dosages for delivery at two or more different predetermined periods.

11. The device of claim 1, further configured to sample an intra-oral substance in the patient's mouth, whether the intra-oral substance has been delivered to or is already present in the mouth; and diagnose a body condition based on a result of the intra-oral substance sample.

12. The device of claim 11, wherein the body condition comprises a disease.

13. The device of claim 11, further configured to perform a close-loop delivery of the substance within the mouth based on the result of the intra-oral substance sample.

14. The device of claim 11, further configured to transmit the result of the intra-oral substance sample to a remote computer for diagnosis.

15. The device of claim 1, wherein at least one of the one or more substances contains at least one of the following active ingredients: trypsin; elastase; papain; aminobenzoate potassium; cathepsin; amylolytic enzyme; proteolytic enzyme; celluloytic enzyme; lipase; prostaglandin E2; prostaglandin F2alpha; heparin; relaxin; conconavalen A; nicotine; hyaluronidase; alpha-L-iduronidase; catabolin; estradiol; genipin; carbodiimide; glutaraldehyde; formaldehyde; 1,6-diaminohexane; bioflavonoids; or reducing sugars including glucose, ribose, or derivatives thereof.

16. The device of claim 1, wherein at least one of the one or more substances alters tooth movement by stimulating or reducing bone resorption.

17. The device of claim 1, wherein at least one of the one or more substances contains a bisphosphonate.

18. The device of claim 1, wherein a first reservoir of the one or more reservoirs is supplied with a first substance of the one or more substances and a second reservoir of the one or more reservoirs is supplied with a second substance of the one or more substances.

19. The device of claim 18, wherein the first substance is different from the second substance.

20. The device of claim 18, wherein the first substance is the same as the second substance.

21. The device of claim 18, wherein a third reservoir of the one or more reservoirs is supplied with a third substance of the one or more substances, wherein the first and third substances are different from the second substance.

22. The device of claim 1, wherein one of the one or more substances comprises analgesics.

23. The device of claim 1, wherein the nozzle is configured to be inserted into the gum on a lingual side of the number of teeth.

24. The device of claim 1, wherein the nozzle is configured to be inserted into the gum on a frontal side of the number of teeth.

25. The device of claim 24, wherein the dental device includes a second nozzle configured to be inserted into the gum on a lingual side of the number of teeth.

26. The device of claim 1, wherein a dispensing mechanism of the nozzle is chemically activated.

27. The device of claim 1, wherein a dispensing mechanism of the nozzle is electronically activated.

28. The device of claim 1, wherein the dental device includes a processor thereon for controlling a dispensing mechanism of the nozzle.

29. A system for delivering one or more substances, comprising:
a plurality of appliances, comprising shells formed of a material, configured to move a number of teeth of a patient, wherein at least one of the appliances includes:
a reservoir formed in the shell; and
a nozzle formed of the material as a portion of the shell, connected to the reservoir, and configured to be inserted into a gum of the patient to fluidly release a substance from the reservoir at a first preselected dose at a first predetermined time period and to fluidly release the substances from the reservoir at a second preselected dose at a second predetermined time period, wherein the nozzle is shaped to conform to the gum for prolonged placement therein.

30. The system of claim 29, wherein the plurality of appliances are designed from scans of the patient's dentition.

31. The system of claim 30, wherein at least one of the plurality of appliances is designed to dispense a plurality of substances in a predetermined sequence.

32. The system of claim 30, wherein two or more of the plurality of appliances are designed to dispense the substance in two or more different preselected dosages for delivery at two or more different predetermined periods.

33. The system of claim 29, wherein the reservoir is supplied with the substance.

34. The system of claim 29, wherein the nozzle is configured to be inserted into the gum on a lingual side of the number of teeth.

35. The system of claim 29, wherein the nozzle is configured to be inserted into the gum on a frontal side of the number of teeth.

36. The system of claim 35, wherein the at least one of the appliances includes a second nozzle configured to be inserted into the gum on a lingual side of the number of teeth.

37. The system of claim 29, wherein a dispensing mechanism of the nozzle is chemically activated.

38. The system of claim 29, wherein a dispensing mechanism of the nozzle is electronically activated.

39. The system of claim 29, wherein the at least one appliance includes a processor thereon for controlling a dispensing mechanism of the nozzle.

40. The system of claim 39, wherein the processor is configured to control the dispensing mechanism of the nozzle in a close-loop manner.

41. The system of claim 29, wherein the shell includes a cavity shaped to be removably placeable over a number of teeth.

* * * * *